(12) United States Patent
Mohon et al.

(10) Patent No.: US 11,547,521 B2
(45) Date of Patent: Jan. 10, 2023

(54) AEROSOL CONTAINMENT APPARATUS, SYSTEMS AND METHODS

(71) Applicant: AirSolve LLC, Albuquerque, NM (US)

(72) Inventors: Barbara Jean Mohon, Santa Fe, NM (US); Janice E. Gallegos, Albuquerque, NM (US); Justine Gabriela Humble, Albuquerque, NM (US); Jordan Blaize Humble, Albuquerque, NM (US)

(73) Assignee: AirSolve LLC, Albuquerque, NM (US)

( * ) Notice: Subject to any disclaimer, the term of this patent is extended or adjusted under 35 U.S.C. 154(b) by 96 days.

(21) Appl. No.: 17/031,872

(22) Filed: Sep. 24, 2020

(65) Prior Publication Data

US 2022/0087774 A1 Mar. 24, 2022

(51) Int. Cl.
*A61B 90/40* (2016.01)
*A47C 1/02* (2006.01)
*A47C 1/06* (2006.01)
*A47C 1/11* (2006.01)

(52) U.S. Cl.
CPC ............ *A61B 90/40* (2016.02); *A47C 1/02* (2013.01); *A47C 1/06* (2013.01); *A47C 1/11* (2013.01)

(58) Field of Classification Search
CPC ........ A61G 10/04; A61G 10/005; A61G 1/04; A61M 16/0627
See application file for complete search history.

(56) References Cited

U.S. PATENT DOCUMENTS

| 2,915,074 A | * | 12/1959 | Cameto | ................... | E04H 15/20 |
| | | | | | 52/2.21 |
| 3,000,379 A | * | 9/1961 | Viers | ..................... | A61G 10/04 |
| | | | | | 128/205.26 |
| 3,813,092 A | | 5/1974 | Foster | | |
| 4,885,000 A | | 12/1989 | Hogan | | |

(Continued)

FOREIGN PATENT DOCUMENTS

| CN | 2621625 Y | 6/2004 |
| CN | 1539394 A | 10/2004 |

(Continued)

OTHER PUBLICATIONS

International Search Report and Written Opinon form the International Searching Authority, on PCT No. PCT/US2021/051839, filed Sep. 24, 2020.

(Continued)

*Primary Examiner* — Sarah B Mcpartlin
(74) *Attorney, Agent, or Firm* — Franklin & Associates International Inc; Matthew F. Lambrinos

(57) ABSTRACT

Aerosol containment apparatus and methods of use are provided herein. The apparatus provides for creating an interior rest space for a person. The apparatus includes a self-sealable cover which is configurable to seal the interior rest space for use in dental care, cosmetic care or other procedures. Access to the person is provided by arm ports located on the apparatus. These arm ports are flexible and allow for vertical, horizontal and angular arm movement procedures. The apparatus includes a partially or substantially transparent cover for visual access to the client and an internal utility tray for tool storage. The apparatus, also includes, an air filtration port equipped with a replaceable air filter.

18 Claims, 9 Drawing Sheets

(56) References Cited

U.S. PATENT DOCUMENTS

| | | | |
|---|---|---|---|
| 4,949,714 A * | 8/1990 | Orr | A61M 16/0627 |
| | | | 128/200.24 |
| 4,976,320 A | 12/1990 | Polan | |
| 5,019,031 A | 5/1991 | Towfighi | |
| 5,316,541 A | 5/1994 | Fischer | |
| 5,832,919 A | 11/1998 | Kano et al. | |
| 6,899,668 B2 | 5/2005 | Paranjpe | |
| 7,503,890 B2 | 3/2009 | Kubicsko et al. | |
| 10,016,252 B1 | 7/2018 | Ide et al. | |
| 10,251,801 B2 * | 4/2019 | Breegi | A61B 90/40 |
| 11,229,501 B2 * | 1/2022 | Vizulis | A61G 10/005 |
| 2014/0316455 A1 | 10/2014 | Gnanashanmugam et al. | |
| 2016/0070061 A1 | 3/2016 | Fasano et al. | |
| 2016/0107006 A1 | 4/2016 | Giulianotti et al. | |
| 2016/0113829 A1 | 4/2016 | Poenisch et al. | |
| 2016/0136024 A1 | 5/2016 | Poenisch et al. | |
| 2018/0303691 A1 | 10/2018 | Heyerdahl | |
| 2021/0244594 A1 | 8/2021 | Dougherty et al. | |
| 2021/0315758 A1 * | 10/2021 | Bui | A61G 10/02 |

FOREIGN PATENT DOCUMENTS

| | | | |
|---|---|---|---|
| CN | 1256922 C | 5/2006 | |
| DE | 851240 A | 10/1952 | |
| JP | 3688351 B2 | 8/2005 | |
| KR | 20190096647 A | 8/2019 | |
| WO | WO-2022008917 A1 * | 1/2022 | A61G 10/005 |
| WO | 2022066972 A1 | 3/2022 | |

OTHER PUBLICATIONS

Amber Spradley, Portable inflatable enclosure system with filtered positive pressure gas fed therein, SGMC builds new protective shield for COVID-19 patients, Apr. 3, 2020, p. 1-3, p. 2, Fig. 1, WCTV Eyewitness News, South Georgia Medical Center, Retrieved on May 19, 2020: https://www.wctv.tv/content/news/SGMC-builds-new-protective-shield-for-COVID-19-patients-569365731.html.

B. Babu, S. Gupta, V. Sahni, Aerosol box for dentistry, British Dental Journal, May 8, 2020, p. 1, Fig. 1, British Dental Journal, Chandigarh, India, Retrieved on May 19, 2020: https://www.nature.com/articles/s41415-020-1598-3.pdf.

Dr. Gyorys, (EN) Isolation protecting means of endotracheal intubation and shielding case for fuliminating infections disease in respiratory system, Apr. 7, 2020 p. 1, Fig. 1 , Subsidiary hospital of Zunyi M, 223 Eugene ST North Catasauqua, PA, US 18032, Retrieved on May 19, 2020: https://www.facebook.com/Lehigh-Dental-327417991569/videos/this-is-dr-gyorys-aerosol-tent-he-put-together-he-named-it-the-dartdentalaerosol/699853780786160/?.

ISW Desk, Patient Isolator, Scientists develop Aerosol restricting Canopy for Dental Procedures, May 4, 2020, p. 1-3, p. 1, Fig. 1, Delih Post, India, Retrieved on May 19, 2020: https://delhipostnews.com/scientists-develop-aerosol-restricting-canopy-for-dental-procedures/.

US Army Doctor AAAS, US Army doctor invent COVID-19 isolation chamber to protect hospital staff, Apr. 21, 2020, p. 1-3, p. 1, Fig. 1 Techlink, Bethesda, Maryland, US, Retrieved on May 19, 2020: https://www.eurekalert.org/pub_releases/2020-04/t-uad042120.php.

U of Birmingham, Protective device for performing cranial autopsies, Innovative pop-up tent could be latest line of defence for forontline NHS staff treating patients with COVID-19, Apr. 7, 2020, p. 1-3, p. 1, Fig. 1, The Pennsylvania research corporation, Edgbaston, Birminghan B15 2TT, United Kindom, Retrieved on May 19, 2020: https://www.birmingham.ac.uk/news/latest/2020/04/pop-up-tent-for-frontline-nhs-staff.aspx.

* cited by examiner

AEROSOL CONTAINMENT APPARATUS, SYSTEMS AND METHODS

CROSS-REFERENCE TO RELATED APPLICATIONS

N/A

TECHNICAL FIELD

Some aspects of the present technology are directed to aerosol containment apparatus and, in particular but not exclusively, to aerosol containment apparatus for mitigating transmission of aerosols between a first person and a second person in close proximity to the first person whilst the first person is receiving care from the second person. Some aspects of the present technology are directed to aerosol containment methods, in particular but not exclusively, to aerosol containment methods for mitigating transmission of aerosols, such as but not limited to, viral aerosols between a first person and a second person in close proximity to the first person whilst the first person is receiving care from the second person In some embodiments of the aspect(s) of the present technology, the care is dental care. In some other embodiments of the aspect(s) of the present technology, the care is medical health care. In some other embodiments of the aspect(s) of the present technology, the care is cosmetic care. In some other embodiments of the aspect(s) of the present technology, the care is personal care. In some embodiments, the personal care is beauty and/or cosmetic personal care. In some other embodiments of the aspect(s) of the present technology, the care is non health care.

SUMMARY

According to some aspects, the present technology is directed to an aerosol containment apparatus. In some embodiments the aerosol containment apparatus comprises an upper body rest section, a barrier surround sidewall and an upper body shield cover. In the open configuration of the apparatus, the upper body shield cover may be in an open position and uncovers the barrier surround sidewall. In the closed configuration of the apparatus: the upper body shield cover head region may be in a closed position over and cooperates with the barrier surround sidewall in sealed contact therewith and covers at least a head rest region of the upper body rest section, an overhanging portion may overhang the barrier surround sidewall open end and, optionally over the back rest section, the skirt portion is sealed to the barrier surround sidewall, the upper body rest section together with the barrier surround wall and the upper body shield cover define an interior resting space, and the overhanging portion has a shape and form such that, when the upper body of a person is resting on the upper body rest section in the resting space, the overhanging portion has a free edge in sealed contact with part of the person to thereby seal off the interior resting space from the exterior of the apparatus. Upper body shield cover may be self-sealable to the barrier surround sidewall and the person.

Any one or combination of the technical features of the following embodiments may be combined with the aerosol containment apparatus.

In some embodiments, the aerosol containment apparatus may comprise an upper body rest section for resting thereon the upper body of a person; wherein the upper body rest section comprises a head rest region and back rest region; wherein the upper body rest section is integrated with, or configurable on, the back rest of a chair; a barrier surround sidewall sealed with the upper body rest section; wherein the barrier surround sidewall extends on and around an outer part of the head rest region and has an open end traversing the upper body rest section; wherein the barrier surround sidewall has at least one arm port hole, an upper body shield cover integrated with, attached or attachable to the barrier surround sidewall, wherein the upper body shield cover comprises a head region and an overhanging portion, wherein the overhanging portion comprises a skirt portion; wherein the barrier surround sidewall and/or the upper body shield cover includes at least one arm port hole wherein the apparatus is configurable between an open configuration and a closed configuration; wherein in the open configuration the upper body shield cover is in an open position and uncovers the barrier surround sidewall; and wherein in the closed configuration: the upper body shield cover head region is in a closed position covering at least the head rest region of the upper body rest section and cooperating with the barrier surround sidewall in sealed contact therewith, wherein the overhanging portion overhangs the barrier surround sidewall open end, wherein the skirt portion is sealed to the barrier surround sidewall, wherein the upper body rest section, the barrier surround wall and the upper body shield cover define an interior resting space, and wherein the skirt portion has a shape such that, when the upper body of a person is resting on the upper body rest section in the resting space, the skirt portion is in sealed contact with an upper body part of the person to thereby seal off the interior resting space from the exterior of the apparatus.

In some embodiments, the chair is a recliner chair, such as but not limited to a dental chair, medical heath chair, beauty cosmetic care chair or acupuncture chair.

in some embodiments, a utility tray is fixed or integrated with the underside of the upper body shield cover; wherein in the closed configuration, the utility tray occupies the interior resting space and is accessible via the at least one arm port hole.

In some embodiments, the upper body shield cover is attached to the barrier surround sidewall and moveable between the open and closed positions.

In some embodiments, skirt portion has a free outer edge, wherein at least part of the free outer edge has or is configurable to have a profile corresponding to the profile of the upper body of the a person and wherein in the closed configuration, when the upper body of a person is resting on the upper body section in the interior resting space, the free outer edge is overlapping and in contact with the person and forms a seal therewith.

In some embodiments, the skirt portion comprises a flexible sheet material such as but not limited to medical grade silicone. In some embodiments, the flexible sheet includes material on the outer perimeter which is thicker and/or heavier than the rest of the flexible sheet material.

In some embodiments, the skirt portion has opposing sides and a central region therebetween, wherein the skirt portion has a rear edge, wherein the rear edge comprises opposing side regions and a central region between the rear edge opposing side regions, and wherein each of the skirt portion rear edge opposing side regions is releasably attachable to respective opposing sides of the barrier surround sidewall open end.

In some embodiments, overhanging portion includes a projection portion extending from the upper body shield cover head region; the projection portion projecting over the open end of the barrier surround sidewall; and wherein the skirt portion is sealed or sealable with the projection portion.

In some embodiments, the upper body cover head region and projection portion are a rigid structure.

In some embodiments, each of the skirt portion opposing sides includes an armhole slit.

In some embodiments, in the closed configuration, when the upper body of a person is resting on the upper body rest section, the skirt portion is sealed to the projection portion and the barrier surround sidewall open end, and wherein the skirt portion free front edge is in sealed contact with and overlaps the front of the torso of the person and wherein the skirt opposing sides are wrapped under and in sealed contact with respective sides of the torso allowing the arms of the person to extend out of the sealed interior space via the respective armhole slits whilst maintaining the interior resting space sealed.

In some embodiments, a rivet system releasably attaches the skirt region rear edge central region to the projection portion and the skirt region rear edge opposing side regions to respective sides of the barrier surround sidewall open end. In some embodiments, the skirt portion is releasably attached by other attachment systems.

In some embodiments, the skirt portion is releasably attached to the cover head region without a projection portion.

In some embodiments, the head region together with the projection portion comprises at least partially dome shape.

In some embodiments, upper body shield cover head region together with the projection portion is substantially transparent.

In some embodiments, the barrier surround sidewall includes a flexible sheet material such as but not limited to medical grade silicone.

In some embodiments, the barrier surround sidewall comprises an open ended rigid frame and the flexible sheet material is releasably attached thereto by a rivet system. In some embodiments, the barrier surround sidewall flexible sheet material includes a thicker or reinforced outer perimeter.

In some embodiments, at least one flexible arm port is incorporated in the flexible sheet material of the barrier surround sidewall and/or the skirt portion.

In some embodiments, at least one air filtration port extends through the upper body shield cover between an interior side and exterior side of the upper body shield cover.

In some embodiments, an air filtration system is incorporated in any one or combination of the upper body shield cover, the barrier surround sidewall and the upper rest section, the air filtration system comprising an air inlet port with an air inlet filter and an air outlet port with an outlet filter; wherein each of the air inlet port and air outlet port communicate between the interior resting space and the exterior; and wherein the inlet filter is configured to pull/push air from the exterior through the air inlet port into the interior resting space and/or wherein the outlet filter is configured to pull/push air out through the air outlet port from the interior resting space to the exterior.

In some embodiments, the air filtration system is incorporated into the cover head region and/or projection portion.

In some embodiments, an adjustable strap system is integrated with or attachable to the bottom of the upper body rest section, wherein the adjustable strap system is adjustable to strap and secure the upper body rest section to a back rest of the chair.

In yet other aspects of the present technology, a kit of parts for assembling any one or combination of the embodiments of the apparatus is provided. The kit of parts comprises the parts of the apparatus of any one or combination of the embodiments and optionally: a box or bag, and/or an instruction manual for assembling the apparatus from the kit of parts. The apparatus parts and the instruction manual maybe carried in the box or bag. The kit of parts, on assembly, provide an apparatus according to any one of combination of the embodiments and which is configurable between the open configuration and the closed configuration.

In yet some other aspects, a barrier surround sidewall flexible sheet is provided. The barrier surround sidewall flexible sheet is a flexible sheet according to any one of the embodiments disclosed herein for use with the aerosol containment apparatus.

In yet some other aspects, a skirt portion flexible sheet is provided. The skirt portion flexible sheet is a flexible sheet according to any one of the embodiments disclosed herein for use with the aerosol containment apparatus.

The systems and methods disclosed herein can be embodied in a means for arrangement and/or steps for configurations in some embodiments.

In yet some other aspects of the present technology, methods of operating the aerosol containment apparatus of any one or combination of embodiments are provided. The method may comprise or include configuring the aerosol containment apparatus on a chair, and manually configuring the apparatus between the open configuration and the closed configuration.

BRIEF DESCRIPTION OF THE DRAWINGS

The accompanying drawings, where like reference numerals refer to identical or functionally similar elements throughout the separate views, together with the detailed description below, are incorporated in and form part of the specification, and serve to further illustrate embodiments of concepts that include the claimed disclosure, and explain various principles and advantages of those embodiments.

The methods and systems disclosed herein have been represented where appropriate by conventional symbols in the drawings, showing only those specific details that are pertinent to understanding the embodiments of the present disclosure so as not to obscure the disclosure with details that will be readily apparent to those of ordinary skill in the art having the benefit of the description herein.

DETAILED DESCRIPTION OF PREFERRED EMBODIMENTS

Figure 1:
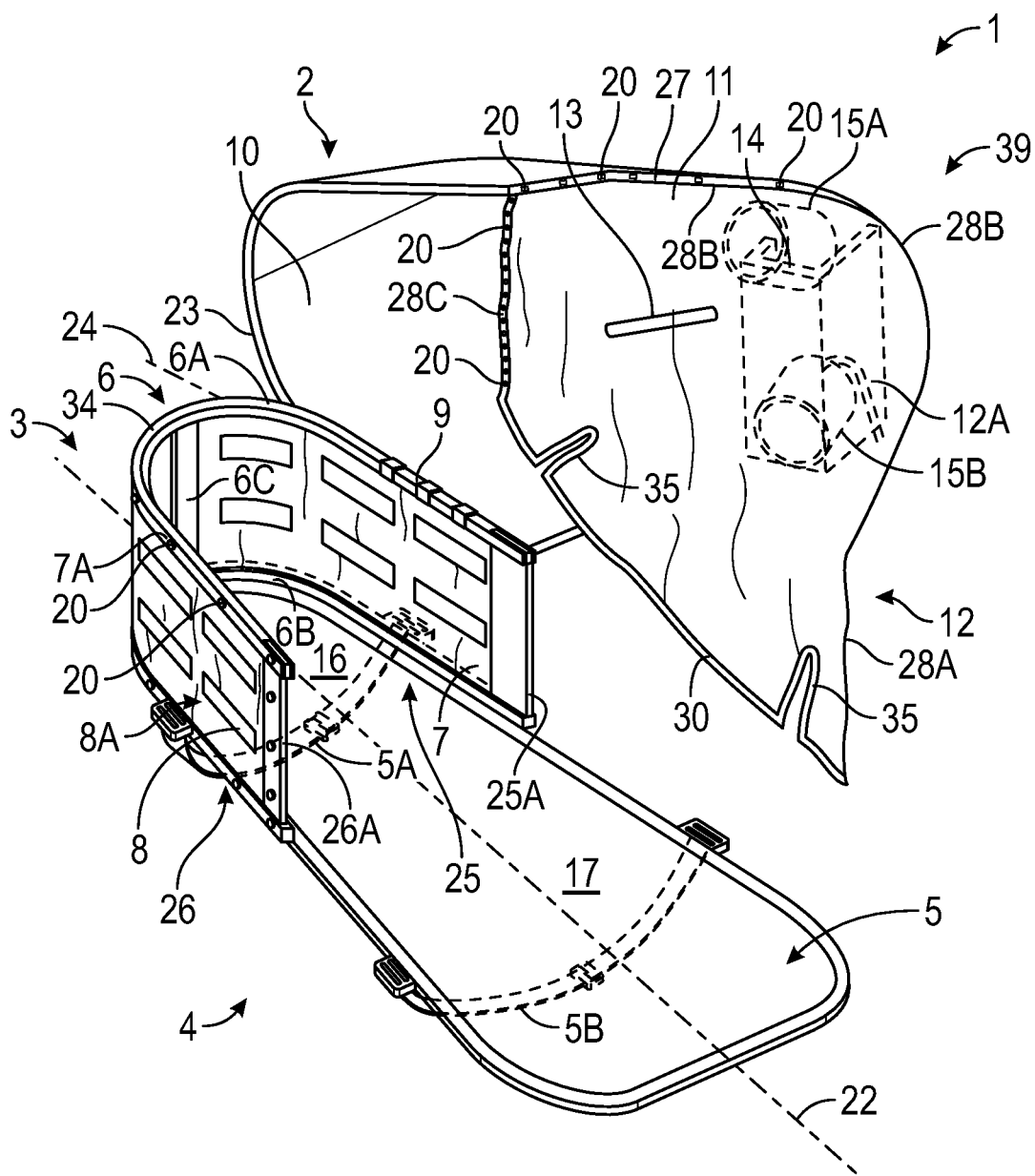
FIG. 1 depicts a front right perspective view of the aerosol containment apparatus in the open configuration in accordance with an embodiment of the present technology.

In the following description, for purposes of explanation and not limitation, specific details are set forth, such as particular embodiments, procedures, techniques, etc. in order to provide a thorough understanding of the present technology. However, it will be apparent to one skilled in the art that the present technology may be practiced in other embodiments that depart from these specific details.

The terms "seal" is used herein to mean a seal that is sufficient to eliminate or substantially mitigate aerosol transmission through the seal. Similarly, "sealed" or "sealable" is used herein to mean sealed or sealable to the extent sufficient to eliminate or substantially mitigate aerosol transmission through the resulting seal.

Technical features described in this application can be used to construct various embodiments of aerosol containment apparatus, systems and/or methods for mitigating transmission of viral aerosols and/or other aerosols between a first person and a second person in close proximity to the first person whilst the first person is receiving care from the second person. Such aerosols may be in the form of but not limited to aerosolized particles and/or droplets. Such viral aerosols may comprise coronavirus aerosols, such as covid 19 aerosols but viral aerosols may be aerosols from any type of virus. Furthermore, such aerosols may comprise or include bacteria and/or fungal aerosols. By way of example, such aerosols my comprise or include dental aerosols.

As a general outline, the aerosol containment apparatus of the present technology according to some aspects is attachable to or integrated with a chair and configurable between an open configuration and a closed configuration. In the open configuration, an upper body shield cover uncovers at least a portion of a upper body rest section of the apparatus whereas in the closed configuration the upper body shield cover cooperates with a barrier surround sidewall in sealed or sealable contact therewith and covers at least a head rest region of the upper body rest section such that the upper body rest section, the barrier surround wall and the upper body shield cover define an interior resting space. A skirt portion of the upper body shield cover has a shape such that, when the upper body of a person is resting on the upper body rest section in a resting space, the skirt portion is in sealed contact or sealable with part of the person to thereby seal the interior resting space from the exterior of the apparatus. Skirt portion may be self-sealable to the barrier surround sidewall and a person.

By way of example, in order to more adequately explain the present technology, reference will be made in more detail hereinafter to one approach of the present technology in which dentistry aerosol containment apparatus, systems and/or methods are configured to mitigate transmission of aerosols between a first person and a second person in close proximity to the first person whilst the first person is receiving dental care from the second person. However, in some other approaches of the present technology, the aerosol containment apparatus, systems and/or methods are other types of health care apparatus, systems and/or methods configured to mitigate transmission of aerosols between a first person and a second person in close proximity to the first person whilst the first person is receiving other the other types of health care, such as but not limited to medical heath care, from the second person. In yet some other approaches, the aerosol containment apparatus, systems and/or methods are configured to mitigate transmission of aerosols between a first person and a second person in close proximity to the first person whilst the first person is receiving personal care, such as but not limited personal cosmetic care (beauty care etc.), or any types of non-health care.

Reference will now be made to the drawings in which the various elements of embodiments will be given numerical designations and in which embodiments will be discussed so as to enable one skilled in the art to make and use the invention.

Specific reference to components, process steps, and other elements are not intended to be limiting. Further, it is understood that like parts bear the same reference numerals, when referring to alternate Figures. It will be further noted that the Figures are schematic and provided for guidance to the skilled reader and are not necessarily drawn to scale. Rather, the various drawing scales, aspect ratios, and numbers of components shown in the Figures may be purposely distorted to make certain features or relationships easier to understand.

As will be made more apparent hereinafter, in the figures, the chair is a dentistry chair and the aerosol containment apparatus includes technical features that allow a person, such as a dentist, in close proximity to a person resting on the dentistry chair, to provide dental care to the person resting on the chair. It will be understood that in some approaches the aerosol containment apparatus is not limited to the chair whilst in some other approaches the aerosol containment apparatus may be integrated in the chair and limited to such an arrangement. It will also be understood that in accompany figures, the aerosol containment apparatus is not limited to the chair but is being shown in the figures in its operable configurations on the chair for the purpose of explaining the configurations of the apparatus. Furthermore, it will be understood that the person resting on the chair and the person providing dental care are not part of the embodiments shown in the accompany figures but are being illustrated to show how the different configurations of the aerosol containment apparatus can be used in dentistry.

Figure 2A:
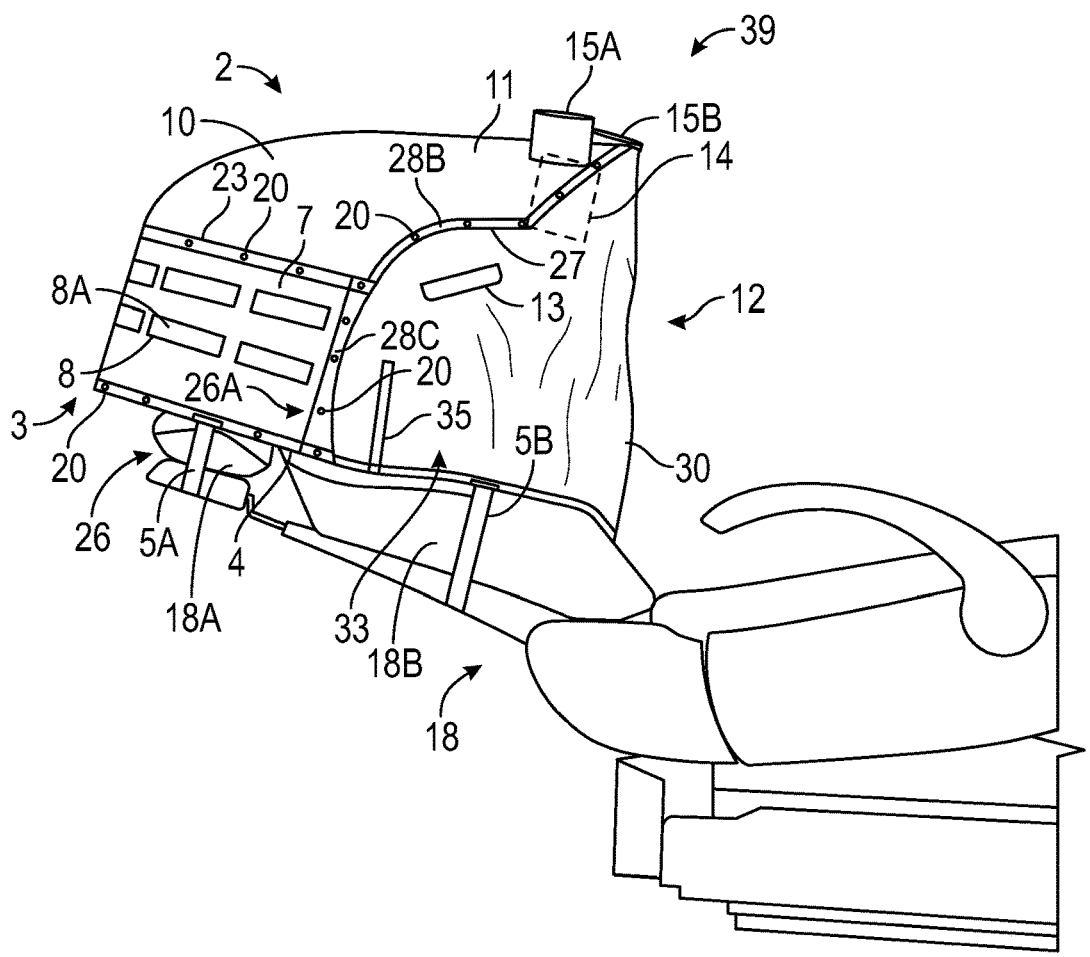
FIG. 2A depicts a rights side elevation view of the aerosol containment apparatus of FIG. 1 installed on a chair with the upper body shield cover closed.

Referring in more detail to the accompanying figures, FIG. 1 is a right side perspective view taken from above of an aerosol containment apparatus 1 according to one embodiment and FIG. 2A illustrates a right side view of the apparatus in FIG. 1 attached to a chair. Broadly, aerosol containment apparatus 1 has a containment upper body shield cover 2, barrier surround sidewall 3, and upper body rest section 4, Barrier surround sidewall 3 is sealed with upper body rest section 4. Apparatus 1 is configurable between an open configuration and a closed configuration. In the open configuration, cover 2 is in an open position and an overhanging portion 39 of cover 2 is detached from barrier surround sidewall 3 as shown for example in FIG. 1. FIG. 2A illustrates cover 2 is closed over barrier surround sidewall 3 and cover overhanging portion 39 is attached to barrier surround side wall 3.

Upper body rest section 4 is configured to enable the upper body of a person 50 to rest comfortably thereon when the apparatus is attached to the chair 18. Upper body rest section 4 is a substantially rigid structure that takes a planar elongated form. In the embodiment of the apparatus 1 of FIG. 1, upper body rest section 4 is a board made from ridged material sandwiched by memory foam pads with a covering, such as faux. However, any substantially planar rigid structure capable of serving as an upper body rest section 4 when attached to a chair may be adopted. Upper body rest section 4 has a head rest region 16 and back rest region 17 and is dimensioned to accommodate the upper body of a person resting thereon. The periphery of head rest region 16 is generally u-shaped and opposite linear sides of upper body rest section 4 flare outwardly from head rest region 16 to back-rest region 17. When apparatus 1 is attached to chair 18, upper body rest section 4 can be laid over chair head and back rests 18A,18B such as for example as shown in FIG. 2A. Chair 18 is a reclining dentistry chair but in some other embodiments, chair back rest 18B may be fixed in a reclined or substantially horizontal or vertical position and/or the chair may be a different type of chair.

As shown in FIG. 1, barrier surround sidewall 3 is attached to head rest region 16 and arranged generally symmetrically with respect to the longitudinal central axis 22 of upper body rest section 4. The length of barrier surround sidewall 3 extends circumferentially around the periphery of head rest region 16. The height of barrier surround sidewall 3 extends generally perpendicular to the longitudinal plane in which upper body rest section 4 extends from head region 16 to back region 17. In this manner, barrier surround sidewall 3 has a flared substantially U-shaped configuration with opposing legs 25, 26 extending along opposite sides of head rest region 16 and has an open end traversing upper body rest section 4 between head rest region 16 and back rest region 17. As will be made more apparent below, since barrier surround sidewall 3 does not extend all the way along back rest region 17, there is less bulk in the area surrounding a person 50 resting on upper body rest section 4. This has some advantages including providing more room for an operator 51 to sit or stand and maneuver their arms in relation to person 50 and allows easier access into and out of the apparatus by person 50.

Barrier surround sidewall 3 is made of a rigid structure sufficient to support upper body shield cover 2. In the embodiment of the apparatus shown in FIG. 1, barrier surround sidewall 3 is made up of a flared substantially u shaped open ended rigid skeleton frame 6 and a replaceable flexible sheet material 7, extending lengthwise in the flared substantially U shape, covering along the exterior side of frame 6.

Frame 6 is made from a rigid material such as plastic or metal. In some other embodiments, barrier surround sidewall 3 may be constructed from a single component or material. For example, the single component could be molded with thin and thick volumes such that it provides structural integrity to support upper body shield cover 2 as well as flexibility in areas along barrier surround sidewall 3.

Frame 6 is made up of a top frame part 6A, bottom frame part 6B and a neck frame part 6C, intermediate between top and bottom frame parts 6A,6B. Top frame part 6A is a flared substantially U-shaped rod. Top frame 6A has a square cross section. However, in some other embodiments, other shaped cross sections may be used. Top frame part 6A provides the barrier surround sidewall top peripheral side 34 which extends in a flared substantial U shape from one end of barrier surround sidewall 34 to the opposing end. Top peripheral side 34 has a flat sealing surface. Bottom frame part 6B has a shape generally corresponding to top frame part 6A and serves as the bottom peripheral side of barrier surround side wall 3. Neck frame part 6C is aligned with the symmetric axis of barrier surround wall 3 and extends generally upright from the longitudinal plane of upper body rest section 2. Opposite ends of neck frame part 6C interconnect spaced apart respective apexes of top frame part 6A and bottom frame part 6B such that the top and bottom frame parts 6A,6B are substantially aligned one above the other in spaced apart substantially parallel planes. In this manner, the flared substantially U-shaped skeleton frame 6 is formed. Frame 6 is permanently attached to upper body rest section 4 by way of glue, riveting or other permanent attachment means. In some other embodiments, upper body rest section 4 is releasably attached to frame 6.

In some other embodiments, skeleton frame 6 may be formed from other shaped parts that together with flexible material 7 form a generally U-shaped barrier surround sidewall. In some other embodiments, barrier surround sidewall 3 need not be flared. In yet some other embodiments, the U shape may have linear rather than curved sides such as a truncated square or rectangle or may take other regular or irregular shapes that provide a generally openended form. In yet some other embodiments, the barrier surround wall legs 25,26 extend further forwardly over back rest region 17. By way of example, barrier surround sidewall may be an elliptical shape with one end truncated to form the open end. In yet some other embodiments, barrier surround sidewall 3 and upper rest section 4 are integrated together rather than being formed separately and sealed together. By way of example, the chair head res 18At and chair back rest 18B serve as upper body back rest section 4 and barrier surround sidewall 3 is permanently or releasably attached to chair head rest 18A and chair back rest 18B by way of a snap attachment system, rivet system, or other attachment means.

Figure 2B:
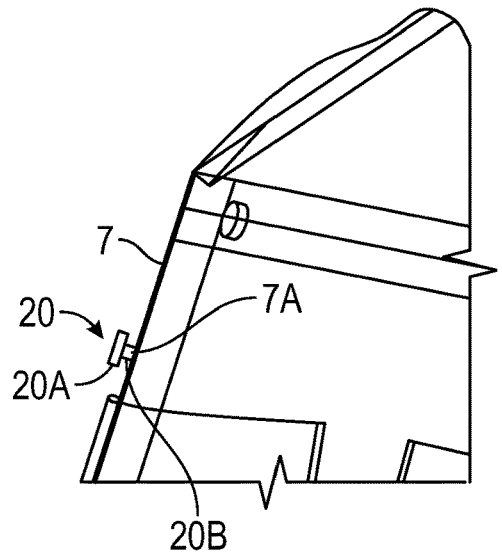
FIG. 2B depicts an enlarged right side elevation view of part of the barrier surround sidewall and cover of the apparatus and chair shown in FIG. 2A.
Figure 10:
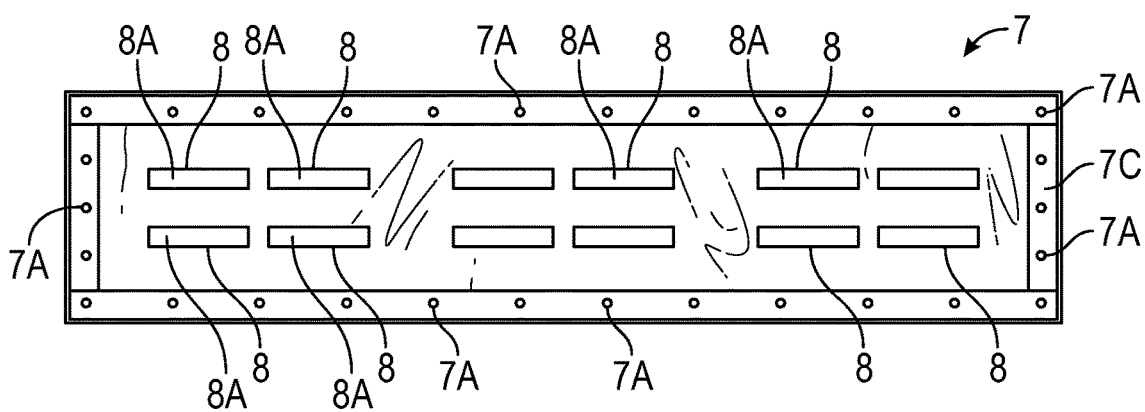
FIG. 10 depicts a top plan view of the flexible sheet material of the barrier surround side wall detached from the frame and laid out flat.

Flexible sheet material 7 is removably sealed to frame 6. In the embodiment of the apparatus 1 shown in FIG. 1, flexible sheet material 7 is releasably attached to frame 6 and sealed thereto by means of a rivet system. FIG. 10 illustrates a top plan view of flexible sheet material 7 detached from barrier surround sidewall 3 and laid out flat. As best shown in FIG. 2A and FIG. 10 taken in conjunction with FIG. 2B, which is an enlarged right side view of a rear part of apparatus 1 shown in FIG. 2A, the rivet system has rivets 20 spaced apart along the exterior side of frame 6 and corresponding holes 7A along the peripheral sides of flexible sheet material 7. The rivet system seals flexible sheet material 7 to frame 6 by interaction of rivets 20 and the holes 7A in a manner that is sufficient to seal flexible sheet material 7 to barrier surround sidewall 3.

These rivets 20 include a distal large diameter 20A and a proximal small diameter 20B. Flexible sheet material 7 includes corresponding holes 7A which are flexible or stretchable around and over the larger diameter 20A and tighten around small diameter 20B to thereby grip rivet 20. Flexible sheet material 7 may be reinforced along the perimeter in the area surrounding the holes 7A such as by making the material thicker (see border 7C in FIG. 10), if desired for decreasing or avoiding damage to the flexible sheet material 7. In this manner, flexible sheet material 7 is sealably attached to cover 2 around frame 6 by means of rivets 20 inserted through respective corresponding holes 7A. Flexible sheet 7 is removable from frame 6 by stretching holes 7A over and off respective corresponding rivets 20 located on frame 6. In some embodiments, flexible sheet 7 has indents or caps formed in the flexible sheet exterior instead of through holes and that are sufficient to stretch over and grip respective rivets and enable skirt portion 12 to be release ably attached.

The rivet system allows frame 6 and flexible sheet material 7 to be removed, cleaned separately from the apparatus and then replaced, or in some cases allows a new or cleaned replacement flexible sheet material 7 to be installed. The flexibility of the flexible sheet material 7 allows for a larger range of horizontal and vertical angled arm movements within the apparatus via arm port holes formed in the flexible sheet material than would be afforded using a barrier surround sidewall made from an entirely rigid material.

Flexible sheet material 7 is a thin silicone sheet material, such as Medical Grade Silicone at 1.5 mm, which allows for good mechanical flexibility and is able to withstand high temperatures. Withstanding high temperatures allows for easier cleaning and sanitation. In some other embodiments, other thickness and/or other flexible sheet materials may be adopted such as but not limited to other types of rubber or plastic, or fabrics. In yet some other embodiments, barrier surround sidewall 3 is entirely rigid structure for applications in which the more limited range of arm movement afforded by the flexible sheet is not critical to the application.

Furthermore, in some other embodiments, other types of sealably attachment systems may be used to releasably seal flexible sheet 7 to frame 6 other than a rivet system. By way of example, in some other embodiments, the sealable attachment system is a zipper system, a releasable adhesive system, or a zip lock type track system. Advantageously, the rivet system, enables flexible sheet material 7 to be removably attached for easy cleaning or replacement of a damaged or contaminated flexible sheet material. Furthermore, the rivet system allows flexible sheet 7 to be autoclavable.

Since upper body rest section 4 is integrated with barrier surround sidewall 3, this allows the sealing interfaces of the apparatus to be completely separated from chair 18.

Barrier surround sidewall 3 supports upper body shield cover 2. Upper body shield cover 2 is configurable between the open and closed positions. When the apparatus is in the open configuration, upper body shield cover 2 is open and uncovers at least a portion of the upper body rest section 4, as shown in for example in FIG. 1, to allow a person 50 to enter apparatus 1 and lay their upper body down on upper rest section 4. When upper body shield cover 2 is closed, cover 2 sealably cooperates with barrier surround sidewall 3 and, together with barrier surround sidewall 3 and upper rest section 4, defines an interior resting space 21 in which the upper body of a person 50 can rest lying down.

As will be explained in more detail below, upper body shield cover 2 has a shape and form such that, when apparatus 1 is in a closed configuration and the upper body of person 50 is resting on upper body rest section 4 in interior resting space 21, cover 2 is in sealed contact with the upper body of person 50 and seals interior resting space 21 from the exterior of the apparatus 1. This sealed interior resting space 21 limits aerosol leakage from the person 50 to a specific small unit versus escaping to the environment.

Upper body shield cover 2 has a head region 10 and an overhanging portion 39. Upper body shield cover 2 has a longitudinal central axis that is substantially aligned with the symmetric axis of the barrier surround sidewall 3. Head region 10 includes a bottom rim 23 at its base that is shaped to cooperate with the top peripheral side 34 of barrier surround sidewall 3. Consequently, the base of head region 10 is profiled and dimensioned such that head region bottom rim 23 has a generally flared substantially U shape profile that complements the shape of top peripheral side 34 of the barrier surround sidewall 3 (see in particular FIGS. 1 and 7).

Figure 8:
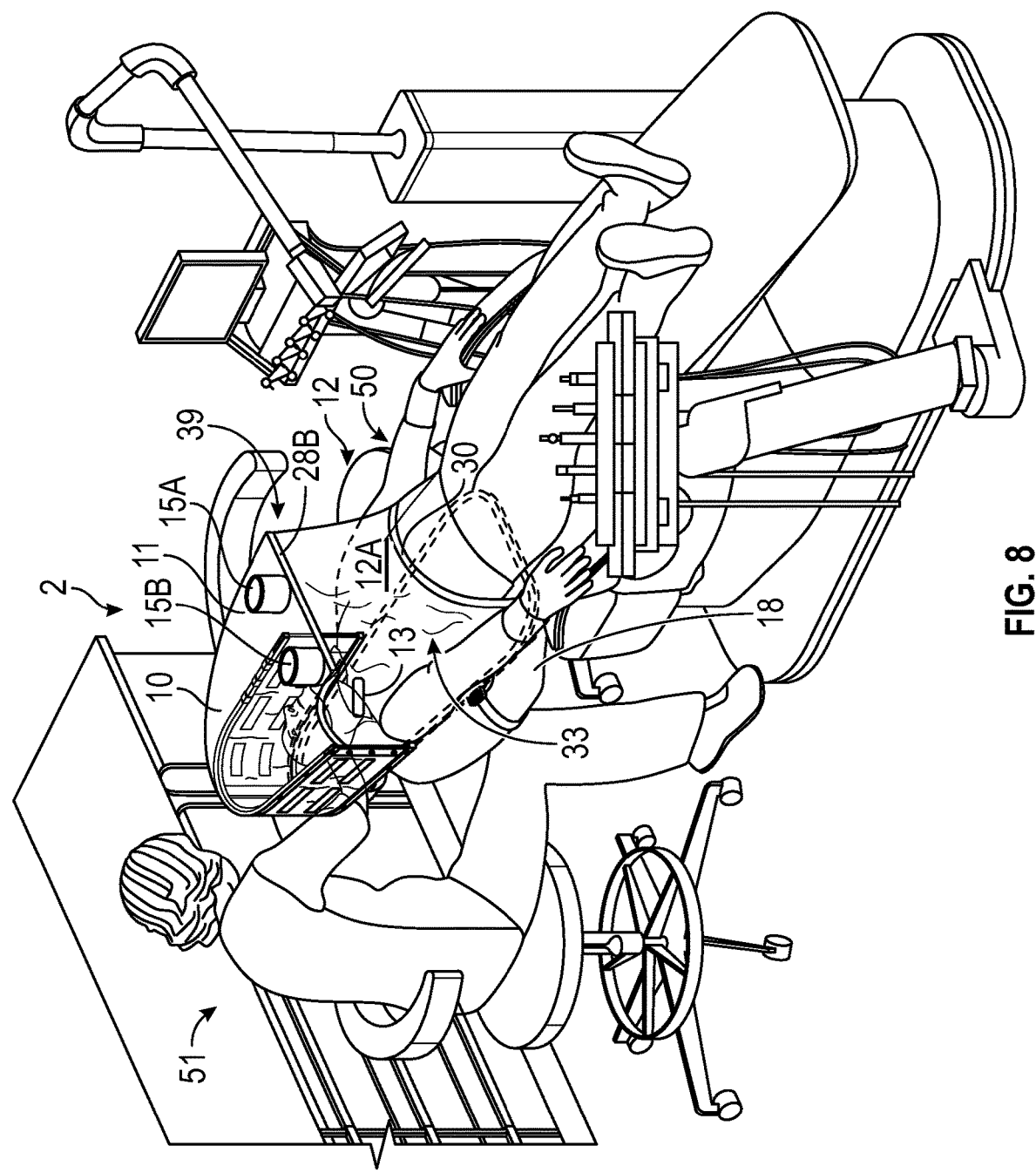
FIG. 8 depicts a right-side front perspective view of the aerosol containment apparatus attached to a chair and in a closed configuration.

Upper body shield cover 2 is moveably attached to barrier surround sidewall 3 such that when cover 2 is open, cover 2 is disposed away from barrier surround sidewall 3 and such that when cover 2 is closed, cover 2 covers over barrier surround sidewall 3 with head region bottom rim 23 sealably cooperating with top peripheral side 34 (see in particular FIG. 2A & FIG. 8). Head region bottom rim 23 and top peripheral side 34 have complementary mating surfaces that seal when cover 2 is closed over barrier surround sidewall 3. In the embodiment of the apparatus 1 of FIG. 1, these complementary mating surfaces are substantially parallel flat surfaces. In some other embodiments the top peripheral side 34 includes a channel or groove for receiving and sealing head region bottom rim 23 to top peripheral side 34. Any shaped complementary surfaces are envisaged that achieve an adequate seal. Opposite ends of head region bottom rim 23 are substantially aligned with respective opposite ends of top peripheral side 34 of barrier surround sidewall 3.

Figure 6:
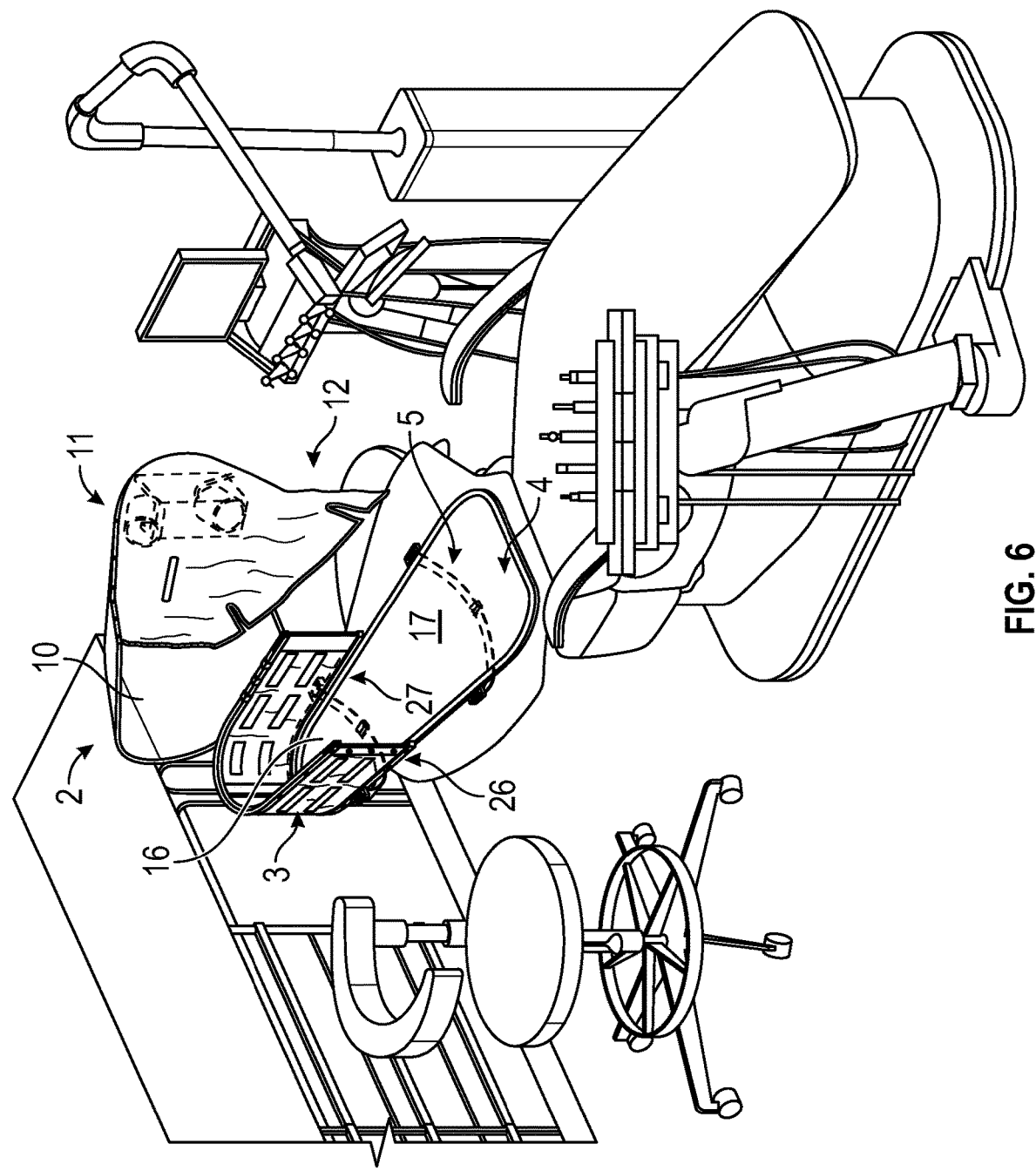
FIG. 6 depicts a right front side perspective view of the aerosol containment apparatus in the open configuration and attached to the chair.

In the embodiment of the apparatus 1 of FIG. 1, cover 2 is moveably attached to barrier surround sidewall 3 by a hinge attached between one side of cover head region bottom rim 23 and one barrier surround sidewall leg 25 as shown in FIG. 1. Hinge 9 interconnects a length of top peripheral side 34 with a corresponding length of head region bottom rim 23 (left leg 25 is on the right side as observed in FIG. 1 and is hinged to cover head region rim 23 but in some embodiments hinge 9 can be joined to the other opposing leg 26 of the barrier surround sidewall and opposite end of head region bottom rim 23. Providing the axis of rotation of the hinge 9 to extend along one of the legs 25,26 of barrier surround sidewall 3 allows upper body shield cover 2 to have a rotational axis extending generally longitudinally of the apparatus but offset to one side. In this manner, upper body shield cover 2 is able to swing approximately 90 degrees or more about the hinge between the closed position and an open position in which the upper body shield cover 2 is to one side of both barrier surround side wall 3 and upper body rest section 4 and out of the way to one side of chair 18 as shown for example in FIG. 6. Advantageously, person 50 can easily position themselves onto upper body rest section 4 while the apparatus is in the open configuration and then it is easy for operator 5 to move cover 2 to the closed position.

In some other embodiments, upper body shield cover 2 is rotatably or pivotally attached to barrier surround sidewall 3 in other positions on barrier surround side wall 3 such that upper body shield cover 2 is pivotable between a different or similar open position and the closed position. Furthermore, in yet some other embodiments, rather than being rotational attached, upper body shield cover 2 is moveably attached in other ways to barrier surround sidewall 3, such as but not limited to attachments that allow linear movement, such that upper body shield cover 2 is movable to the closed position from a similar or different open position.

Upper body shield cover 2 further includes a projection portion 11 that extends from head region 10 (see in particular FIG. 2A). In the embodiment of the apparatus 1 of FIG. 1, cover head region 10 together with projection portion 11 are formed from one piece of rigid material and together form an irregular semi-dome shape that is generally elongated. When cover 2 is closed, cover head region 10 is aligned above barrier surround sidewall 3 and arches upwardly from base bottom rim 23 to cover barrier surround side wall 3. Projection portion 11 extends from cover head region 10 further forwardly and upwardly above and beyond barrier surround sidewall 3 and over back rest section 17 such that projection portion 11 over hangs barrier surround sidewall opposing legs 26, 25 (See in particular FIGS. 2A, 5, 7 and 8). Projection portion 11 has a bottom rim 27 that extends from one end of head region bottom rim 23 to the other. Opposite ends of projection portion bottom rim 27 project upwardly from respective opposite ends of bottom rim 23 to meet at the top of a forward most part of projection portion 11 that is disposed generally along symmetric axis of barrier surround sidewall 3. In this manner, when cover 2 is closed, projection portion bottom rim 27 extends between opposing ends of top peripheral side 34 of the barrier surround side wall 3.

Projection portion bottom rim 27 has a profile whereby opposite ends initially arch upwardly and forwardly in a concave shape from respective opposing ends of bottom rim 23, reach a turning point and then arch further forwardly, upwardly and inwardly in a convex shape until they meet at the top of the projection portion 11 (see in particular FIG. 2A). Projection portion bottom rim 27 may have other profiles that extend between opposing ends of the head region bottom rim 23. When upper body shield cover 2 is closed, the top of front sides 25A, 26A of barrier surround side wall legs 25, 26 are substantially aligned with respective opposite ends of projection portion bottom rim 27 such that barrier surround sidewall front ends 25A,26A together with head projection portion bottom rim 27 and a surface of upper body rest section 24, generally define a boundary or perimeter around interior space 21 that is sealable.

In some embodiments, head region 10 and projection portion 11 are substantially made of plexi-glass that is at least partially transparent. This plexi-glass head region 10, is an advantage for operator 51 as it provides for visual access into the interior resting space 21. The projection portion 11 also being transparent is an additional advantage as it allows the operator 51 to see further inside and around the interior resting space 21 and so have an improved view of the person's head. In some other embodiments, cover head region 10 and cover projection portion 11 may be separate pieces that have been fixed together and formed from the same or different rigid materials. Furthermore, in some other embodiments, head region 10 and/or projection portion 11 may take the form of other shapes that provide a sufficient boundary around an interior space for person 50 resting on upper back rest section 4 and that have a base that cooperates with barrier surround sidewall 3 when cover 2 is closed.

Figure 7:
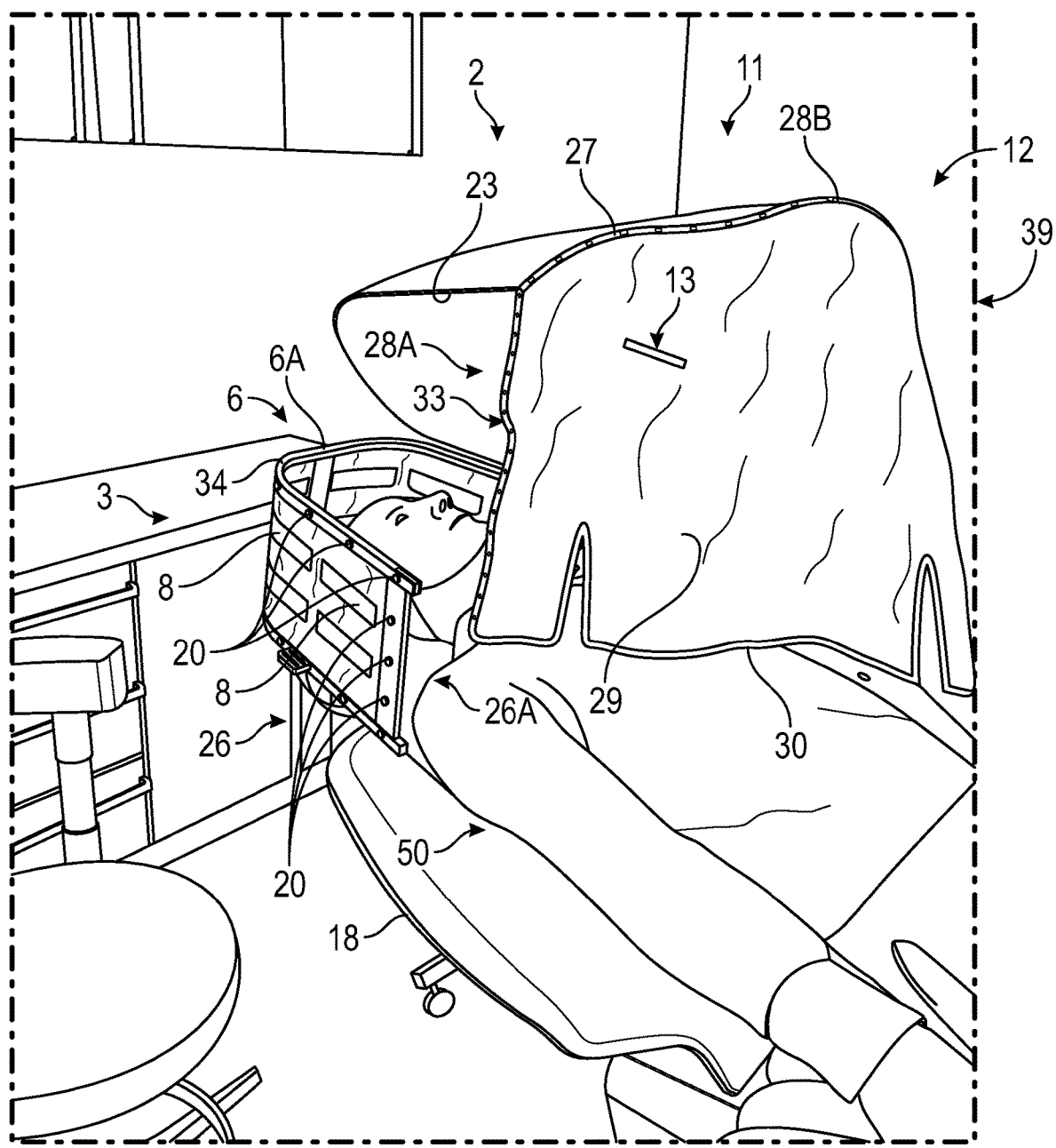
FIG. 7 depicts a right front side perspective view of the aerosol containment apparatus attached to a chair and with the upper body shield cover partially closed and the upper body of a person inside the apparatus.
Figure 9:
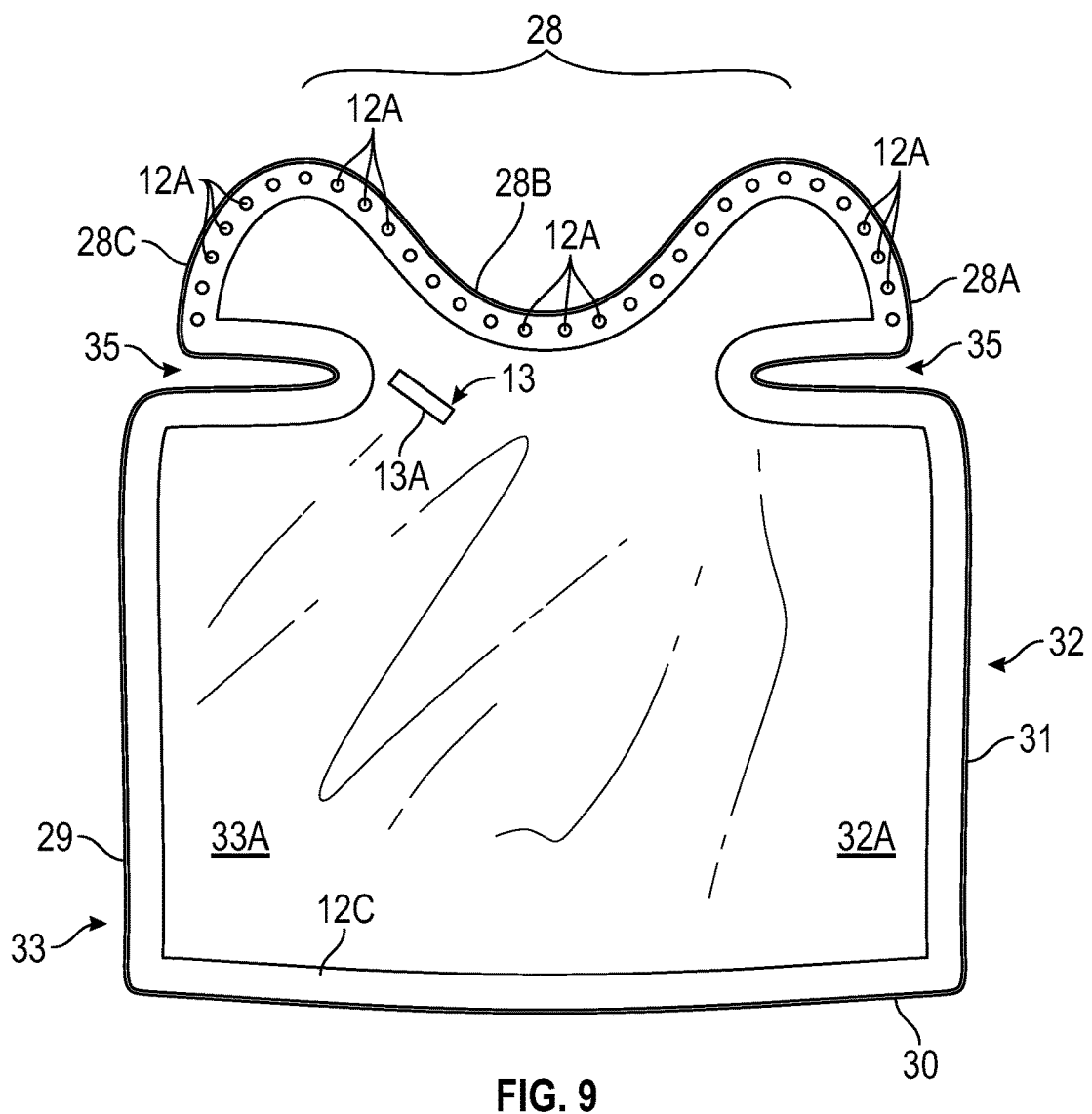
FIG. 9 depicts a top plan view of the skirt portion flexible sheet material detached from the cover projection portion and barrier surround sidewall of the apparatus of FIG. 1 and laid out flat.

A skirt portion 12, together with projection portion 11 forms, overhanging portion 39 which is the part of cover 2 that overhangs barrier surround sidewall legs 25, 26. Skirt portion 12 is formed from flexible sheet material and releasably attached to projection portion 11. A top plan view of the skirt portion flexible sheet material detached from the apparatus and laid out is shown in FIG. 9. Skirt portion flexible material is a similar material and thickness to flexible sheet material 7. In some other embodiments, skirt portion flexible sheet material is a different material and/or thickness to flexible sheet material 7. When cover 2 is closed or near closed over barrier surround sidewall 3, skirt portion sheet material hangs and is configurable such that when a person is lying in the rest position, the sheet material is configurable to form a shape having a narrower front open end and a wider rear open end (see for example FIG. 8 in which the skirt portion is configured to have a quasi half frusto conical shape). As indicated in FIG. 7 taken in conjunction with FIG. 9, rear edge 28 has central region 28B replaceably attached along the length of the projection portion bottom rim 27. Opposite rear edge regions 28A, 28C are unattached to projection portion 11 and extend freely downwardly from respective opposite sides of rear edge central portion 28B. A front region of skirt portion 12 slopes downwardly from projection portion 11 to front free edge 30. When upper body shield cover 2 cover is closed over person 50, front free edge 30 is configurable to form a concave sealing edge over the torso of person 50 and generally traverses the longitudinal symmetric axis 22 of upper rest section 4

In the embodiment of the apparatus 1 shown in FIG. 1, skirt portion 12 is made from flexible sheet material that is sufficiently flexible to allow the skirt portion sheet material to hang and deform naturally such that skirt portion 12 can be draped by hand and adjusted to frame the upper body of person 50 when apparatus 1 is in the closed configuration. The skirt portion flexible sheet material may be silicone which allows for good mechanical flexibility and able to withstand high temperatures. About 1.5 mm or thicker silicone allows for autoclaving, flexibility and durability. Being as soft/flexible as possible is desirable so therefore silicone as thin as 1.5 mm may be adopted although thicker sheets are envisaged in some other embodiments. Withstanding high temperatures allows for easier cleaning and sanitation. In some embodiments, skirt portion 12 is made from medical grade silicone sheet material.

Skirt portion 12 has opposing sides 32,33 (left and right sides) extending between the front free edge 30 and rear edge 28 of the skirt portion. Skirt opposing sides 32, 33 each have a respective longitudinal free edge 31, 29 (left, right) extending rearwardly from a respective opposite end of front free edge 30. Right side free edge 29 terminates at the end of right rear edge 28C. Left side free edge 31 terminates at the end of left rear edge 28A.

Skirt portion 12 is shaped such that when cover 2 is closed, opposite sides 32, 33 hang, or are configurable, lengthwise generally in front of and aligned with respective barrier surround sidewall legs 25,26. Opposite rear edges 28A, 28C complement respective front ends 25A, 26A of barrier surround sidewall legs 25,26. In this manner, skirt portion opposite rear edges 28A, 28C are replaceable attachable to respective front ends 26A, 25A (See for example FIG. 1 taken in conjunction with FIG. 2A and FIG. 7). When rear edges 28A, 28C are so attached, the length of skirt portion rear side edge 28 (right rear edge 28A, central rear edge 28B and left rear edge 28C) is sealed along the length of projection bottom rim 27 together with barrier surround sidewall front ends 26,25 that align with projection portion bottom rim 27. As a result, the entire outer perimeter defined by barrier surround side wall front ends 26, 26B and projection portion bottom rim 27 is sealed by the skirt portion rear edge 28. Skirt portion opposite side free edges 29, 31 together with free front edge 30 form a free sealing edge. As will be explained in more detail below, free sealing edge 29, 30, 31 is configurable to close off the remaining opening into the apparatus when the upper body of person 50 is lying on the upper body rest section 4 and thereby configure the apparatus in the closed configuration.

When a 50 person is resting on upper body rest section 4 and cover 2 is closed, free front edge 30 generally complements the concave profile of a chest or waist of person 50. As best shown in FIGS. 7 & 8, the length of the free front edge 30 is made heavier, such as by making it sufficiently thicker than the rest of the skirt portion sheet, and serves as a weight such that, when the upper body of the person 50 is lying inside the apparatus, the weighted free front edge 30 remains pressed against the person's body as a result of gravity and sealably cooperates with the person's upper body. Thus, free front edge 30 seals against the torso of person 50. Skirt opposing sides 33, 32 are configurable to frame and sealable cooperate with respective right and left sides of the torso. In some embodiments, when skirt portion 12 is made less flexible and is able to maintain a shell like shape but is yet still deformable, other parts of the skirt portion may serve to weight free front edge 30 and free front edge 30 may not need to be thicker than the rest of the skirt portion sheet material.

In the embodiment of the apparatus of FIG. 1, right and left skirt opposing sides 33, 32 each include wrappable flap regions 33A, 32A. Right wrappable flap 33A extends lengthwise from right rear edge 28C to adjacent the right end of front free edge 30. Left wrappable flap 32A extends lengthwise from left rear edge 28A to adjacent the left end of front free edge 30. Left wrappable flap 32A is manually foldable underneath the left side of upper body person 50 lengthwise. Left side longitudinal free edge 31 forms the distal longitudinal edge of the flap 32A. Right wrappable flap 33A is manually foldable underneath the right side of upper body person 50 lengthwise. Right side longitudinal free edge 29 forms the distal longitudinal edge of the flap 33A.

When the skirt portion left and right rear edges 28A, 28C are detached from barrier surround sidewall 3 and cover 2 is open with the skirt central rear edge 28C left attached to projection bottom rim 27, skirt portion flexible material is able to freely hang down in generally vertical planes on the cover hinged side of the apparatus without significantly obstructing entry into the interior space 21 (see FIG. 1). In some other embodiments in which skirt portion sheet material is less flexible, the remainder of skirt portion 12 is sufficiently rigid to maintain its shape and remain extended in the same plane as the rest of cover 2 on the hinged side also without obstructing the apparatus entry.

As upper body shield cover 2 is rotated to close over barrier surround sidewall 3, opposing sides can fall into place along each side of person 50. Left flap 32A is configurable such that when person 50 is lying on the upper rest section, flap 32A is wrappable underneath the left side of the upper body of the person between the person and the upper rest section 4. Similarly, right flap 33A is wrappable underneath the right side of the upper body of the person between the person and upper rest section 4. In this manner, skirt position left side 32 is sealable with the left side of the person's upper body and upper rest section 4 and skirt portion right side 33 of the skirt portion is sealable with the right side of the person's upper body and upper rest section 4.

As best shown in FIGS. 1 & 2A taken in conjunction with FIG. 8, opposing sides 29,31 include respective slits 35 for each arm of person 50. On the right side, slit 35 has an open end at the right side linear free edge 29 and extends generally upwardly to a closed end. On the left side, slit 35 has an open end at the left side linear free edge 31 and extends generally upwardly to a closed end. Each slit 35 is positioned and open ended to allow slit 35 to frame and seal the upper arm of person 50 when cover 2 is in the closed position. In some other embodiments, each or both slits 35 may be a type of slit with both ends closed and person 50 must insert their arms through slit 35 from the interior to the exterior such that the upper body arms are sealed by skirt portion 12. In some other embodiments, one of both of the left and right upper arm slits 35 are omitted and barrier surround sidewall legs and/or skirt portion 12 is shaped such that one or both of the person's arms may be disposed entirely inside the interior space and sealed off by barrier surround sidewall legs and/or skirt portion 12 using the wrappable opposing sides 29, 31.

Apparatus 1 is in a closed configuration when the interior space occupied by the upper body of person 50 is entirely sealed off from the exterior by cover 2. In the closed configuration: skirt opposing rear edges 28A, 28C are attached to respective barrier surround sidewall front ends 25A, 26A to seal off an open area around the shoulder/upper arm of the person, respective slits 35 are sealed around upper arms of person 50, skirt front free edge 30 is sealed to the front of the upper body the person 50, skirt opposing sides 32,33 are wrapped between respective sides of the upper body and upper rest section 4 and sealed to respective opposing sides of the upper body of person 50. Advantageously, the aerosol containment apparatus 1 does not require the use of adhesive for sealing off the interior resting space from the exterior.

Skirt portion 12 is releasably attached and sealed to barrier surround sidewall 3 thereto by means of a rivet system. The rivet system may be similar in operation to the rivet system adopted in the barrier surround sidewall 3 as shown for example in FIGS. 2A & 2B. Rivets 20 are spaced apart along the exterior face of projection portion 11 adjacent projection portion bottom rim 23 and the exterior faces of respective barrier surround sidewall front ends 25A,26A. Skirt portion rear edge 28 includes corresponding through holes 12A. Rivets 20 include a distal large diameter 21A and a proximal small diameter 21B. The skirt portion flexible sheet material includes corresponding holes 12A which flex or stretch around the larger diameter 21A and grip on the small diameter 21B. Skirt portion flexible sheet material is reinforced in the area surrounding the holes, such as by making the material thicker, as required for decreasing damage to the flexible sheet material. Skirt portion rear edge 28 is sealably attached to the projection portion and barrier surround sidewall 3 by means of manually press fitting the flexible sheet holes 12A over corresponding rivets 20 on projection portion 11 and barrier surround sidewall 3. The skirt flexible sheet can be removed by stretching holes 12A over and off corresponding rivets 20. In some embodiments skirt portion 12, has indents or caps formed in the flexible sheet exterior instead of through holes and that are sufficient to stretch over and grip respective rivets and enable skirt portion to be release ably attached.

The rivet system allows skirt portion 12 to be cleaned separately from the remainder of the apparatus or in some cases allows a new or clean replacement skirt portion to be installed. In some embodiments, skirt portion central rear edge 28B may be attached to projection portion bottom rim 23 by an attachment system that is different from the rivet system used to attach the right and left skirt opposing rear edge sides 28C, 28A to barrier surround sidewall front ends 26A, 25A.

Advantageously, since the rivet system or other attachment system enables the flexible sheet material of the skirt portion to be removably attached for easy cleaning or replacement of a damaged or contaminated flexible sheet material, the complete aerosol containment apparatus can be cleaned and/or repaired for reuse.

In some other embodiments, attachments systems other than a rivet system are adopted to releasably attach skirt portion 12 to barrier surround sidewall front ends 25A,26A and/or projection portion 11. In the open configuration, the skirt portion 12 may be entirely detached from projection portion 11. In other embodiments, skirt portion 12 is permanently attached to projection portion bottom rim 23 or even integrated therewith. In some embodiments, skirt portion is permanently attached to projection portion 11 by means of a suitable bonding material. In some other embodiments, rather than being fastened to projection portion 11, skirt portion 12 has a free rear edge that is sealably attached to barrier surround sidewall 3 and/or cover 2 in the closed position by draping skirt portion flexible sheet material rear edge, including the thicker perimeter, of skirt portion 11 over the exterior face of cover 2 (including bottom rim 23 and/or barrier surround sidewall front ends 26A,25A) such that the weight of the skirt portion thicker perimeter and flexible sheet material seals the skirt portion rear edge to cover 2 and/or barrier surround sidewall 3.

In some embodiments, some portions of skirt portion 12 such as the opposing sides and/or flaps may be made from a sheet material that is more flexible than the central region. In some other embodiments, the skirt portion structure is sufficiently stable to maintain its shell-like shape when the skirt central portion is attached in the overhanging position whether the apparatus is in the closed configuration or an open configuration yet has some flex to enable skirt portion to frame and seal with the upper body of the person 50.

Barrier surround sidewall 3 includes at least one arm port hole 8 which is flexible. When apparatus 1 is in the closed configuration. arm port hole 8 allows an operator 51 access to interior resting space 21 whilst maintaining a seal between space 21 and the exterior. This access allows operator 51 to perform dental work without risk of aerosol transmission between person 50 and operator 51.

In the embodiment of the apparatus of FIG. 1, barrier surround side wall 3 includes a plurality of spaced apart flexible arm port holes 8 each of which is formed as an elongated opening or slit and associated flap enclosure. Each elongated opening or slit is oriented to run lengthwise generally parallel with upper rest section 4. The plurality of holes 8 are spaced apart circumferentially around the barrier surround wall and arranged in two spaced rows one above the other. In some other embodiments, the number and arrangement of holes may be different. Furthermore, in some embodiments, arm port holes 8 may be formed in barrier surround wall using different sizes, shapes and/or types of openings.

Additionally, barrier surround sidewall 3 has an associated flexible arm port hole flap 8A that covers and cooperates with art port hole 8, this flap 8A may be used to provide for additionally sealing around the operator's arm. Since arm port hole 8 includes a flap 8A for sealing around an operator's arm, there is no need to integrate a glove into the barrier surround sidewall 3. An arm port hole without an integrated glove feature is advantageous since it provides the option to operator 51 to use thin single use external gloves which the applicant has found are better for tactile sensitivity as required in dentistry. Providing a plurality of arm port holes 8 and associated flaps 8A spaced apart around barrier surround sidewall 3 is advantageous in that operator 51 is able to access various different regions of interior space 21 using different arm port holes 8 selectively with one arm or both arms. Since arm port holes 8 are also located around head rest region 15, this advantageously allows operator 51 easy access to the person's head and/or oral cavity, while sitting or standing. Another advantage of arm port holes 8 with flaps 8A is that they can also be used as ports for dental devices such as suction hoses or air/water syringe devices which are routinely used in dental procedures. In some other embodiments, arm port hole flaps 8A are omitted.

In the embodiment of FIG. 1, arm port holes 8 are formed in the flexible sheet material 7. Since the arm port hole 8 is included in the flexible sheet material 7 making both the arm port hole and associated flap flexible, it allows operator 51 to move his/her arms in horizontal, vertical and angled movements, while maintaining a sealed interior resting space 21. Arm port hole 8A flap enclosure is formed from a thicker flexible material to help strengthen the arm port hole 8.

Furthermore, an arm port holes 13 is included in skirt portion 12, on seal with skirt opposing side 33. In the embodiment of the apparatus of FIG. 1, arm port hole 13 is disposed on skirt portion 12 generally diagonally between slit 35 and central rear edge 28B. Arm port hole 13 is flexible, elongated and provides access to interior resting space 21. An associated arm port hole flap 13A cooperates with arm port hole 13 which allows use of single use gloves which has some advantages as explained above and avoids the need for an integrated glove feature in skirt portion 12. Since arm port hole 13 is disposed in cover 2 rather than barrier surround sidewall 3, it can be spaced further towards the longitudinal central axis of apparatus 1 and forward above the barrier surround sidewall 3 such that operator's arm accessing interior space 21 via arm port hole 13 is able to maneuver an instrument or tool more easily and/or differently into and/or around the mouth of the person than via arm port 8. In some other embodiments, the number and/or position of arm port holes 13 on cover 2 may be different to suit the application. In some embodiments, the arm port hole or holes are positioned in a similar manner and/or differently to facilitate cosmetic treatment such as make up application, eyebrow plucking or facial work or acupuncture treatment. In still other applications, the access could provide for oral or facial surgery. Furthermore, in some other embodiments, any of the arm port holes may have a different shape, size, orientation and have a different means of sealing around the arm than by flaps.

Figure 5:
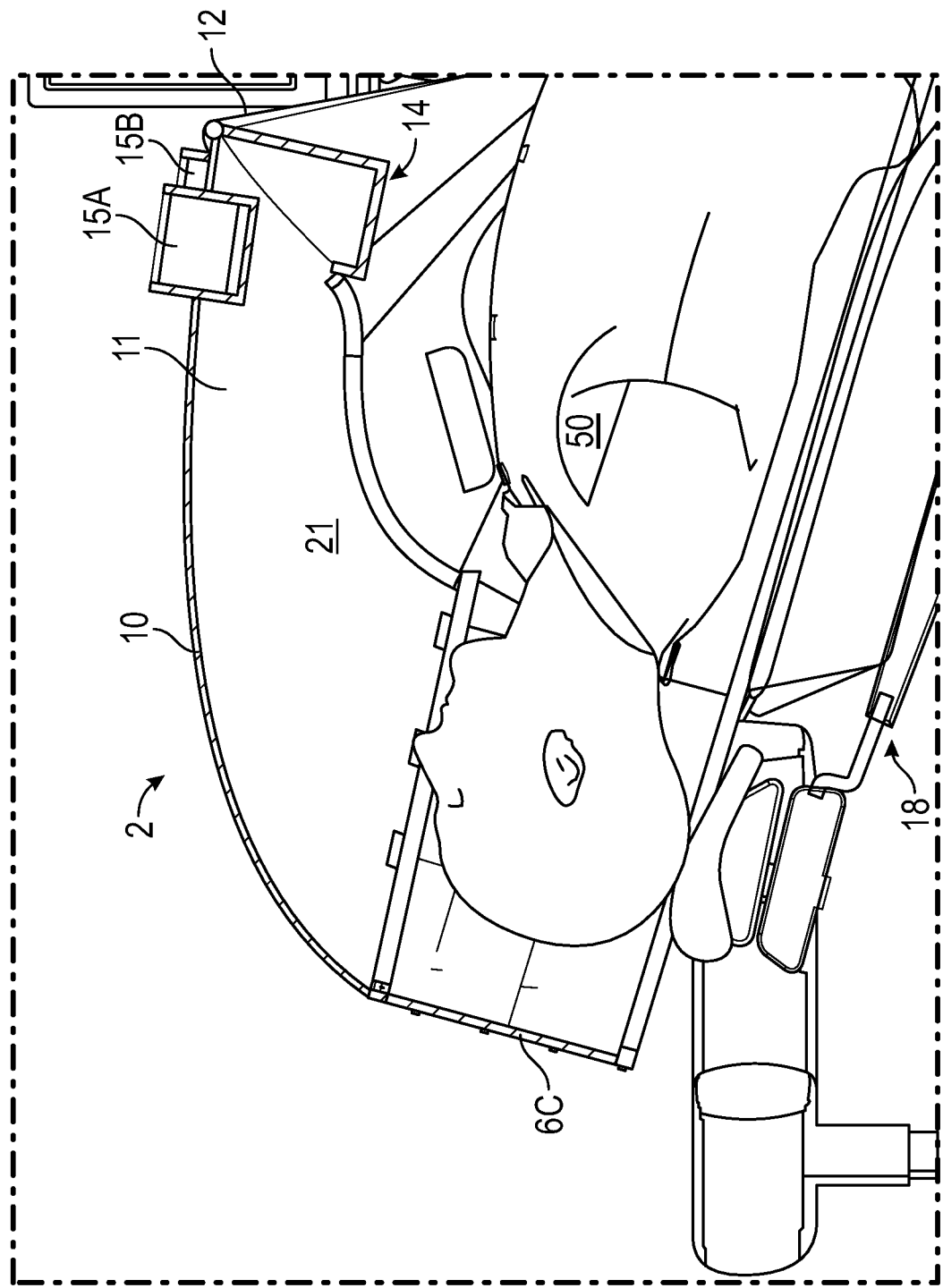
FIG. 5 depicts an enlarged partial cross-sectional view taken along a central longitudinal axis of the aerosol containment apparatus shown in FIG. 4.

Upper body shield cover 2 includes a utility tray 14. As shown in FIG. 1 and in FIG. 5, which is an enlarged cross sectional view of part of the apparatus taken along a central longitudinal axis of apparatus 1, utility tray 14 is integrated with an underside of cover 2 such that it is located entirely within interior resting space 21 and is accessible via one or more of arm port holes 8,13. In the embodiment of the apparatus of FIG. 1, utility tray 14 serves as a dental tray for dental tools or products. In some other embodiments, utility tray 14 may be a cosmetic tray for cosmetic tools and products for cosmetic applications. In some other embodiments, utility tray 14 is a medical tray for medical tools or products. In some other embodiments, utility tray 14 is an acupuncture tray for acupuncture tools or products. As best shown in FIG. 5, utility tray 14 is attached to the underside of cover 2 so that it is located forward of the head of person 50 and above the person's chest when person 50 is lying in interior space 21 and cover 2 is closed. Utility tray 14 is located on the symmetric axis of the cover and is integrated into or fixed to the projection portion 11. Utility tray 14 has a traversally extending base that is oriented such that it is generally in a plane parallel with the upper rest section 4 when cover 2 is closed. Utility tray 14 has support wall which is generally perpendicular to the tray base and interconnects the length of one side of the tray base to the underside of projection portion 12. Internal utility tray 14 allows access by the operator 51 via arm port holes 8,13 to instruments/tools etc. on tray 14 rather than operator 51 having to introduce them into interior space 21 from the exterior or remove them from interior space 21 by breaking the seal to the interior space or by introducing them via arm port holes. This reduces the number of times the operator 51 is required to remove and insert an arm through arm port holes 8,13 reducing wear and tear of the arm port hole 7 and minimizes risk of viral or other infection from contaminated tools/instruments or arms that would otherwise have to be introduced into and removed from the interior space via the arm port holes or by opening the cover.

Utility tray 14 is made from a suitably rigid material such as plastic or metal. Integrating or fixing utility tray 14 to underside projection portion 11 is advantageous in that projection portion 11 is made from rigid plexi glass or other material that is more rigid than skirt portion sheet material. In addition, locating utility tray 14 on projection portion 11 mitigates possible obstruction of the transparent view person 50 has when looking up through cover 2 because utility tray 14 (and operator 51 when accessing or manipulating tools on the tray) are spaced away from the head of person 50. In some embodiments, internal utility tray 14 is integrated with or fixed to other parts of the apparatus such as the barrier surround sidewall 3, upper rest section 4 or skirt portion sheet material 12.

Figure 3:
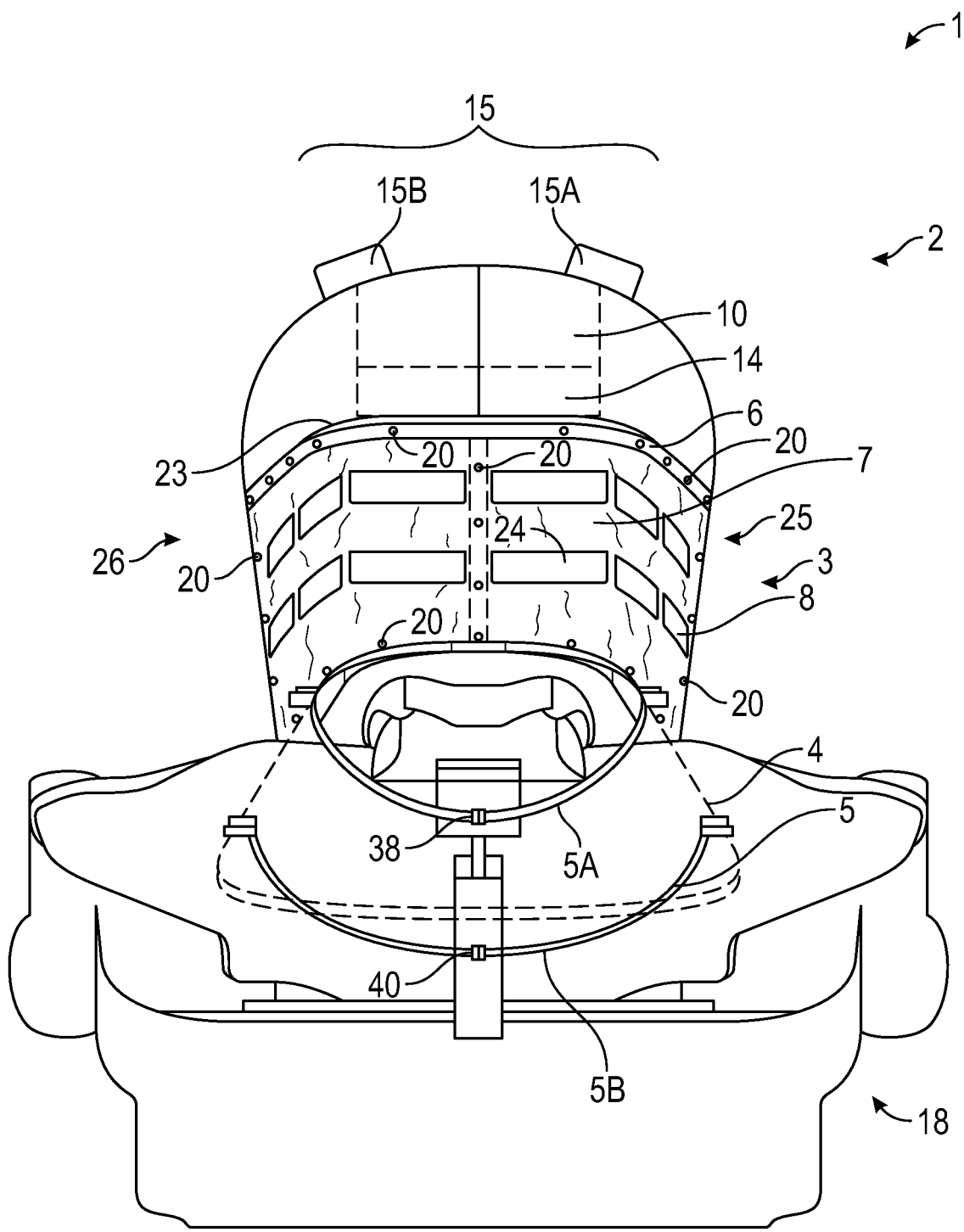
FIG. 3 depicts a rear elevation view of the apparatus and chair shown in FIG. 2A.
Figure 4:
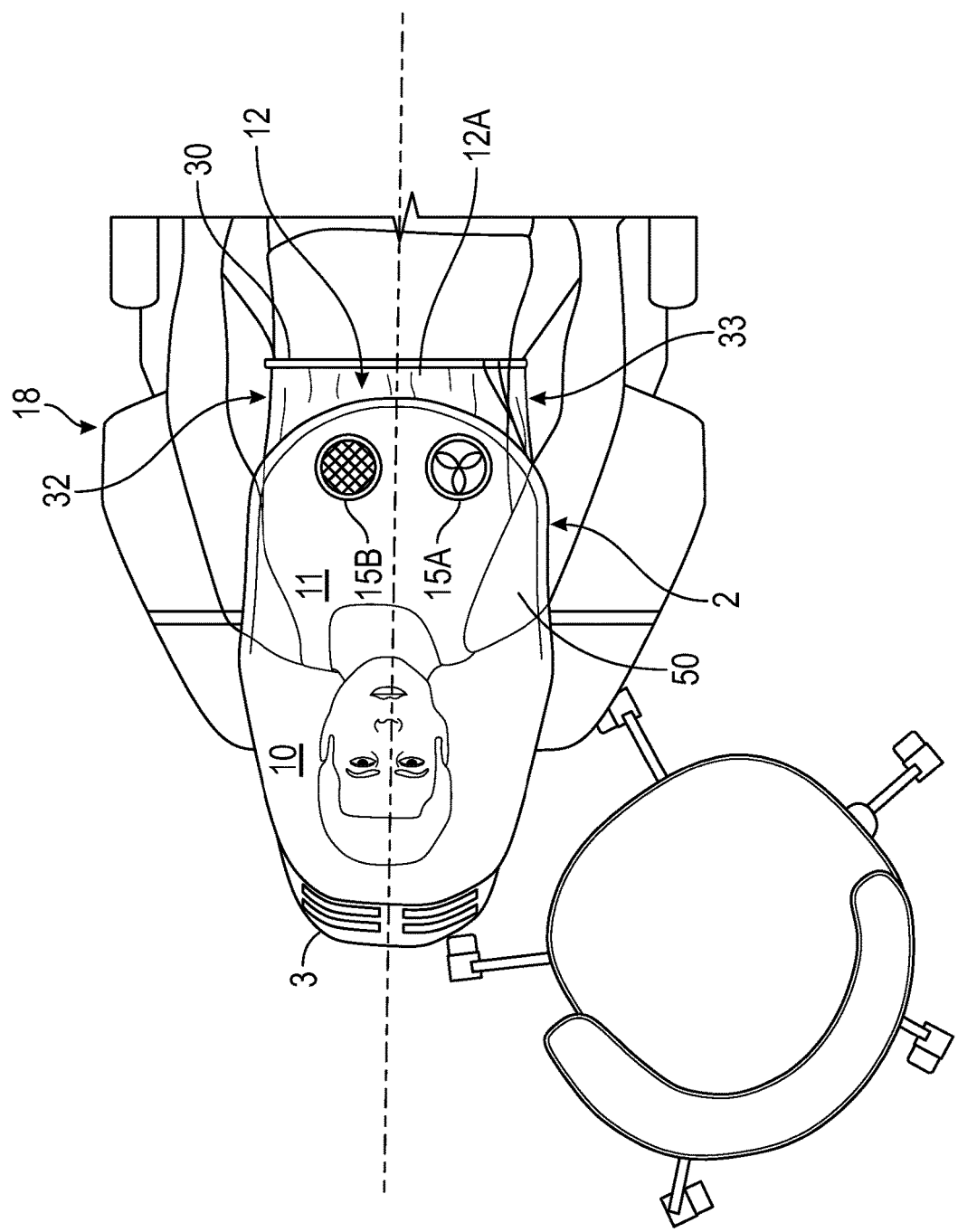
FIG. 4 depicts a top plan view of the aerosol containment apparatus and chair shown in FIG. 2A but with the upper body of a person resting inside the apparatus.

Aerosol containment apparatus 1 is releasably attached to a chair 18 in an operable configuration by a universal chair attachment system. As best shown in FIG. 3 taken in conjunction with FIG. 2A which depict the aerosol containment apparatus 1 integrated with the dental chair, installation of upper body rest section 2 on dental chair 18 is achieved using an adjustable strap system 5 integrated with or attachable to the underside of upper body rest section 2 and bottom of barrier surround sidewall 3. Strap system 5 has a rear adjustable strap 5A that is fixed at opposite ends to the exterior bottom of respective barrier surround side wall legs 25,26. A front adjustable strap 5B is fixed at opposite ends to respective opposite side edges of back-rest section 17. Adjustable strap system 5 is adjustable to strap and secure upper body rest head region 16 to chair head rest 18A and upper body back rest portion 17 to chair back rest 18B. FIG. 1 shows rear and front straps 5A, 5B and corresponding buckles 38, 40 for adjusting straps 5A, 5B to allow integration of upper body rest section 2 with chair 18. Straps 5A, 5B are wrapped around the respective head rest 18A and back rest 18B of the dental chair 18. Buckles 38, 40 secure the respective straps. The strap buckle system is a quick side release buckle system such as for example those found on backpacks. In some other embodiments, the buckle system is a heavy-duty buckle system for a less portable apparatus. In some other embodiments, other buckle systems that have an easy, quick and durable release may be adopted.

Since upper body rest section 2 is attached to the dental chair 18 by a universal strap attachment system, apparatus 1 is attachable to and usable with different types of dental chairs 18. This is an advantage because dental chairs come in many sizes and shapes. Furthermore, as the attachment system is configured to releasably attach apparatus 1 to a chair, it can be removed from a chair and used on a new or different type of chair, or different sized chair, as desired.

An air filtration system 15 is located in cover 2. Air filtration system communicates between the exterior of cover 2 and interior space 21. Air filter system 15 is a self-contained battery operated fan/air purifier that filters air into and out of interior space 21 without the use of external apparatus. The fan/air purifier may be rechargeable. In other embodiments it may be connected to an external power supply to operate. When apparatus 1 is in the closed configuration, it is configured to operate as a positive pressure system in which air is pushed into interior space 21 via a fan in the air filter system inlet 15A communicating between interior space 21 and the exterior. Since interior space 21 is substantially air tight by virtue of cover 2 sealing off interior space 21, any substantial buildup of positive pressure inside interior space 21 is balanced by virtue of air filter system outlet 15B which communicates between interior space 21 and the exterior and which filters air being expelled or vented naturally from interior space 21. Alternatively, the fan is incorporated into outlet 15B and pushes air out of the interior to the exterior and inlet 15A naturally pulls in air to interior space 21 from the exterior.

Air inlet 15A and air outlet 15B and fan/air purifier filters 15C are incorporated into head region of cover 2 which is sufficiently rigid to support them. In some other embodiments, air filter system inlet and/or outlet and associated filters and fan are incorporated in other parts of the apparatus instead of or in addition to cover 2.

In some embodiments, the shape and/or type of the ventilation ports may be different in shape or size than those shown in the accompanying figures. Furthermore, in some embodiments, the outlet port 15B may be a simple exiting vent 15B, virus appropriate, filter material such as n-95 masking material or Hepa filtration material that does not require a tube style port but optionally may be easily attached to a tube with elastic type materials. In some embodiments, the air inlet port 15A may be a simple intake port with filter material in which case air outlet port 15B incorporates the fan for pulling/pushing air out of the interior space to the exterior and air inlet port 15A naturally pulls air into the interior (or vice versa). In some embodiments, both the inlet 15A and the outlet 15B may be simple intake and outtake ports made with filter material and without a fan. In some embodiments both ports 15A,15B can include both a fan and filter, one to pull air into the interior and the other to pull air out of the interior.

In some embodiments, air filter system inlet is configured to receive a hose of an external air filter system (not shown) that is inserted into the inlet to pump air into the interior space and air is either naturally expelled from the outlet through a filter on the cover or via a separate exhaust hose of the external pump system inserted into the outlet. Alternatively, in some embodiments, air filter system outlet is configured to receive a hose of an external air filter system (not shown) that is inserted into the outlet to suck air out of the interior space 21 into the external air filter system and air is naturally drawn into the inlet either through a filter on the cover or via a separate exhaust hose of the external pump system inserted into the inlet to provide filter air from the system. When such external pump systems are used the air filter/fan may be omitted from the inlet or outlet that is intended to be used with an external air system. In some other embodiments, air filtration system may be configurable between an air filter system that is self-contained on the cover and receive a receive a system that comprises air filtration ports for using the apparatus with an external air pump/suction system. In some other embodiments, apparatus 1 has one or more additional air ports or other air passageways that are configurable between a closed state, in which the interior space is maintained entirely sealed except for via the air filtration system, and an open state in which interior space is no longer sealed.

The method of use for the above described embodiment will now be described.

Initially, apparatus 1 must be installed on the chair. In order to install the apparatus on the chair, apparatus 1 is placed on the chair 18 with the upper rest section of the apparatus extending lengthwise and barrier surround sidewall 3 facing away from the chair. Generally, the head region 16 and back region 17 of upper rest section 4 are aligned with head and back rests 18A, 18B respectively of chair 18.

The strap adjustment system is used to secure upper rest section 4 to chair 18 for example as shown in FIGS. 1 to 7. The upper body shield cover 2 is closed while attaching apparatus 1 to chair 18 to make it easier to handle the apparatus. Straps 5A,5B are released from respective buckles 38, 40 and wrapped underneath the respective chair head rest 18A and back rest 18B. Straps 5A, 5B are then attached and tightened around chair 18 using the buckles 38,40 to securely fasten upper body rest section 4 to chair 18.

When cover 2 is still closed, skirt portion central rear edge 28B is releasably attached to the projection bottom rim 27 using the rivet system whereas skirt portion opposing rear edges 28A, 28C are left unattached. This may be done before or after attaching apparatus 1 to chair 18.

The apparatus is now ready for use Upper body shield cover 2 is rotated to the open position by the operator 51 to bring apparatus 1 into the open configuration. Since entry into the chair is unobstructed by cover 2, a person 50 is able to enter the apparatus by sitting on upper back rest section 4 and lying down generally as they would do on chair 18 without apparatus 1 attached. The person's head is now resting on head rest region 15 with their face facing away from the head rest region 15 and their torso resting on the back-rest region 17 of the apparatus 1 (see FIG. 7).

At this point the operator swings the upper body cover shield cover about hinge 9 to close cover 2 (see FIG. 7 taken conjunction with FIG. 8). In doing so, skirt portion 12 hangs around the person's torso. Operator 51 manually configures the skirt portion so that skirt portion slits 35 frame or wrap around respective upper arms/shoulders, front free edge 30 frames across the torso and skirt portion opposing sides 32, 33 are located on either side of the person's torso. Opposing wrappable flaps 32A, 33A are now inserted between the torso and back-rest region 17. Skirt position rear opposing side edges 28A, 28C are attached to respective front ends 25A, 26A of barrier surround sidewall 3. As explained hereinbefore, configuring skirt portion 12 in this manner seals off the remaining opening between the interior space 21 and the exterior (with the exception of air filter system 15 that allows air to transfer between interior space 21 and the exterior). Air filter system 15 is operable to ensure filtering of air to and from interior space 21. The apparatus is now in a closed configuration in which interior resting space 21 is sealed from the rest of the environment and is ready for use by operator 51.

Operator 51 is now able to insert one or more arms into interior resting space 21 via respective arm port holes 8,13 and is able to see the person's head through the transparent head region 10 of cover 2. Operator 51 is able to perform dental procedures using tools on utility tray 14 without breaking the seal between interior space 21 and the external environment. Operator 51 may also insert and remove tools into and out of the interior space via one or more arm ports as needed.

After the operator 51 is finished, opposite rear edges 28A, 28C are detached from respective barrier surround wall front ends 25A, 26A, the inserted opposing wrappable flaps 32A, 33A are pulled out from between the person's torso and the back-rest region 17, and cover 2 is rotated open so that apparatus 1 is in an open configuration. The person 50 is now able to exit from chair 18 without obstruction from cover 2.

As can be understood, apparatus 1 may need to be cleaned after each use, this is especially important if the person may have an infectious decease. As already explained in detail hereinbefore, the apparatus 1 allows for the removal of skirt portion 12 and/or the flexible sheet material 7.

To remove the barrier surround sidewall flexible sheet material 7 and/or skirt portion sheet material, the operator or other user simply stretches the sheet material along an area where rivets 20 and corresponding sheet holes 7A, 12A are located. This enlarges the holes and allows for removal from the corresponding rivets. This eliminates the need for removing or reapplying adhesive as the rivets provide a tight and precise seal.

Both skirt portion 12 and/or the flexible sheet material 7 can now be cleaned or replaced in an appropriate fashion. As indicated, flexible sheet material 7 and skirt portion 12 can be constructed of medical grade silicone and be autoclavable to facilitate cleaning. Additionally, the remainder of apparatus 1 can also be cleaned at this point.

It can be understood that the aerosol containment apparatus of the embodiments described herein may be constructed in small, medium and large sizes. This is simply the nature of the apparatus as it may be configured for adults (large and small) or children.

Additionally, as any one or combination of the flexible sheet material barrier surround sidewall, the skirt portion, and replaceable filters as well as other parts may be replaced, an additional benefit of the aerosol containment apparatus is that these parts are replaceable, thus reducing waste.

Aspects of the aerosol containment apparatus of the present technology provide a universal, self-contained, portable/reusable aerosol containment apparatus that is self-sealing without adhesive, easily cleanable, versatile for use in dental care. cosmetic care, health care and other care environments and operational without the need of external air filtration and/or electrical power systems.

The corresponding structures, materials, acts, and equivalents of all means or step plus function elements in the claims below are intended to include any structure, material, or act for performing the function in combination with other claimed elements as specifically claimed. The description of the present technology has been presented for purposes of illustration and description, but is not intended to be exhaustive or limited to the present technology in the form disclosed. Many modifications and variations will be apparent to those of ordinary skill in the art without departing from the scope and spirit of the present technology. Exemplary embodiments were chosen and described in order to best explain the principles of the present technology and its practical application, and to enable others of ordinary skill in the art to understand the present technology for various embodiments with various modifications as are suited to the particular use contemplated.

In the following description, for purposes of explanation and not limitation, specific details are set forth, such as particular embodiments, procedures, techniques, etc. in order to provide a thorough understanding of the present invention. However, it will be apparent to one skilled in the art that the present invention may be practiced in other embodiments that depart from these specific details.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" or "according to one embodiment" (or other phrases having similar import) at various places throughout this specification are not necessarily all referring to the same embodiment. Furthermore, the particular features, structures, or characteristics may be combined in any suitable manner in one or more embodiments. Furthermore, depending on the context of discussion herein, a singular term may include its plural forms and a plural term may include its singular form. Similarly, a hyphenated term (e.g., "on-demand") may be occasionally interchangeably used with its non-hyphenated version (e.g., "on demand"), a capitalized entry (e.g., "Software") may be interchangeably used with its non-capitalized version (e.g., "software"), a plural term may be indicated with or without an apostrophe (e.g., PE's or PEs), and an italicized term (e.g., "N+1") may be interchangeably used with its non-italicized version (e.g., "N+1"). Such occasional interchangeable uses shall not be considered inconsistent with each other.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

If any disclosures are incorporated herein by reference and such incorporated disclosures conflict in part and/or in whole with the present disclosure, then to the extent of conflict, and/or broader disclosure, and/or broader definition of terms, the present disclosure controls. If such incorporated disclosures conflict in part and/or in whole with one another, then to the extent of conflict, the later-dated disclosure controls.

The terminology used herein can imply direct or indirect, full or partial, temporary or permanent, immediate or delayed, synchronous or asynchronous, action or inaction. For example, when an element is referred to as being "on," "connected" or "coupled" to another element, then the element can be directly on, connected or coupled to the other element and/or intervening elements may be present, including indirect and/or direct variants. In contrast, when an element is referred to as being "directly connected" or "directly coupled" to another element, there are no intervening elements present. The description herein is illustrative and not restrictive. Many variations of the technology will become apparent to those of skill in the art upon review of this disclosure.

While various embodiments have been described above, it should be understood that they have been presented by way of example only, and not limitation. The descriptions are not intended to limit the scope of the invention to the particular forms set forth herein. To the contrary, the present descriptions are intended to cover such alternatives, modifications, and equivalents as may be included within the spirit and scope of the invention as defined by the appended claims and otherwise appreciated by one of ordinary skill in the art. Thus, the breadth and scope of a preferred embodiment should not be limited by any of the above-described exemplary embodiments.

The invention claimed is:

1. An aerosol containment apparatus comprising:
    an upper body rest section for resting thereon an upper body of a person; wherein said upper body rest section comprises a head rest region and back rest region;
    a barrier surround sidewall sealed with the upper body rest section; wherein said barrier surround sidewall extends on and around an outer part of said head rest region and has an open end traversing said upper body rest section;
    an upper body shield cover integrated with, attached or attachable to said barrier surround sidewall, wherein said upper body shield cover comprises a head region and an overhanging portion, wherein said overhanging portion comprises a projection portion and a skirt portion;
    wherein said projection portion extends from said upper body shield cover head region, said projection portion projecting over said open end of said barrier surround sidewall, wherein said skirt portion comprises a flexible sheet material, wherein said skirt portion is sealed or sealable with said projection portion and has opposing sides, a central region therebetween and a rear edge, wherein said rear edge comprises opposing side regions and a central region between said rear edge opposing side regions, wherein each of said skirt portion rear edge opposing side regions is releasably attachable to respective opposing sides of said barrier surround sidewall open end, wherein said skirt portion has a free outer edge, wherein at least part of said free outer edge has, or is configurable to have, a profile corresponding to a profile of an upper body of a person;
    wherein said barrier surround sidewall and/or said upper body shield cover includes at least one arm port hole; and
    wherein said apparatus is configurable between an open configuration and a closed configuration;
    wherein in the open configuration the upper body shield cover is in an open position and uncovers said barrier surround sidewall; and
    wherein in the closed configuration:
    said upper body shield cover head region is in a closed position covering at least the head rest region of the upper body rest section and cooperating with the barrier surround sidewall in sealed contact therewith, wherein said overhanging portion overhangs said barrier surround sidewall open end, wherein said skirt portion is sealed to said barrier surround sidewall, wherein said upper body rest section, said barrier surround wall and said upper body shield cover define an interior resting space, and wherein said skirt portion has a shape such that, when the upper body of a person is resting on said upper body rest section in said interior resting space, said skirt portion is configured to be in sealed contact with an upper body part of the person, wherein the free outer edge is configured to overlap with the person and is further configured to be in contact and to form a seal therewith to thereby seal off the interior resting space from an exterior of the apparatus; and
    further comprising a utility tray fixed or integrated with an underside of said upper body shield cover; wherein in said closed configuration, said utility tray occupies said interior resting space and is accessible via said at least one arm port hole.

2. The apparatus of claim 1, wherein said upper body rest section is configured for use on the back rest of a chair.

3. The apparatus of claim 1, wherein said upper body rest section is integrated with a back rest of a chair.

4. The apparatus of claim 1, wherein the upper body shield cover is attached to the barrier surround sidewall and moveable between the open and closed positions.

5. The apparatus of claim 1, wherein said free outer edge includes material that is thicker and/or heavier than material of the rest of the flexible sheet.

6. The apparatus of claim 1, wherein at least one of said skirt portion opposing sides includes a flexible armhole slit.

7. The apparatus of claim 6, wherein in the closed configuration, when the upper body of a person is resting on said upper body rest section, said skirt portion is sealed to said projection portion and said barrier surround sidewall open end, and wherein said skirt portion free outer edge is configured to be in sealed contact with and overlap a front of the torso of the person and wherein the skirt opposing sides are configured to be wrapped under and to be in sealed contact with respective sides of the torso for allowing the arms of the person to extend out of the sealed interior resting space via the respective armhole slits whilst maintaining the interior resting space sealed.

8. The apparatus of claim 7, wherein a rivet system releasably attaches said skirt region rear edge central region to said projection portion and said skirt region rear edge opposing side regions to respective sides of said barrier surround sidewall open end.

9. The apparatus of claim 8, wherein said head region together with said projection portion comprises at least partially dome shape rigid structure.

10. The apparatus of claim 9, wherein said upper body shield cover head region together with said projection portion is substantially transparent.

11. The apparatus of claim 1, wherein the barrier surround sidewall includes a flexible sheet material.

12. The apparatus claim 11, wherein the barrier surround sidewall comprises an open ended rigid frame and the flexible sheet material releasably attached thereto by a rivet system.

13. The apparatus of claim 12, wherein at least one flexible arm port is incorporated in said flexible sheet material of said barrier surround sidewall.

14. The apparatus of claim 1, further comprising at least one air filtration port extending through said upper body shield cover between an interior side and exterior side of said upper body shield cover.

15. The apparatus of claim 1, comprising an air filtration system incorporated in any one or combination of said upper body shield cover, said barrier surround sidewall and said upper rest section, said air filtration system comprising an air inlet port with an air inlet filter and an air outlet port with an outlet filter; wherein each of said air inlet port and air outlet port communicate between the interior resting space and the exterior; and wherein said inlet filter is configured to pull/push air from the exterior through said air inlet port into said interior resting space and/or wherein said outlet filter is configured to pull/push air out through said air outlet port from the interior resting space to the exterior.

16. The apparatus of claim 15, further comprising an adjustable strap system integrated with or attachable to a bottom of said upper body rest section, wherein said adjustable strap system is adjustable to strap and secure said upper body rest section to a back rest of a chair.

17. The apparatus of claim 1, wherein said upper body rest section is configured for use on the back rest of a recliner chair.

18. The apparatus of claim 1, wherein said upper body rest section is integrated with a back rest of a recliner chair.

* * * * *